(12) United States Patent
Rajasekharan

(10) Patent No.: US 7,229,815 B2
(45) Date of Patent: Jun. 12, 2007

(54) TRIACYLGLYCEROL BIOSYNTHESIS IN THE CYTOSOL OF EUKARYOTES

(75) Inventor: Ram Rajasekharan, Karnataka (IN)

(73) Assignees: Indian Institute of Science, Karnataka (IN); Bijam Biosciences Private Limited, Andhra Pradesh (IN)

( * ) Notice: Subject to any disclaimer, the term of this patent is extended or adjusted under 35 U.S.C. 154(b) by 275 days.

(21) Appl. No.: 10/230,331

(22) Filed: Aug. 29, 2002

(65) Prior Publication Data

US 2003/0157513 A1 Aug. 21, 2003

Related U.S. Application Data

(60) Provisional application No. 60/315,757, filed on Aug. 30, 2001.

(51) Int. Cl.
*C12N 9/14* (2006.01)
(52) U.S. Cl. ..................................................... 435/195
(58) Field of Classification Search ................ 530/300, 530/350; 435/325; 424/94.1
See application file for complete search history.

(56) References Cited

OTHER PUBLICATIONS

Gangar et al. JBC. Mar. 2001; 276:10290-8.*
Wongwathanarat et al. (Microbiology, Oct. 1999;145 (Pt 10):2939-46).*
E. P. Kennedy, "Biosynthesis of Complex Lipids", Federation Proceedings, vol. 20, Dec. 1961, pp. 934-940.
C. Kent et al., "Regulation of Eukaryotic Phospholipid Metabolism", The FASEB Journal, vol. 5, Jun. 1991, pp. 2258-2266.
C. Raetz et al., "Biosynthesis and Function of Phospholipids in *Escherichia coli*", The Journal of Biological Chemistry, vol. 265, No. 3, Jan. 1990, pp. 1235-1238.
K. O. Webber et al., "Dihydroxyacetone Phosphate Acyltransferase", Methods in Enzymology, vol. 209, pp. 92-99.
F. Paltauf et al., "Regulation and Compartmentalization of Lipid Synthesis in Yeast," The Molecular and Cellular Biology of the Yeast Saccharomyces: Gene Expression vol. II, 1992, pp. 415-500.
K. Athenstaedt et al., "Redundant Systems of Phosphatidic Acid Biosynthesis via Acylation of Glycerol-3-Phosphate or Dihydroxyacetone Phosphate in the Yeast *Saccharomyces cerevisiae*", Journal of Bacteriology, vol. 181, No. 5, Mar. 1999, pp. 1458-1463.
S. L. Pelech et al., "Signal Transduction via Phosphatidylcholine Cycles", TIBIS 14, Jan. 1989, pp. 28-30.

Y. Nishizuka, "Studies and Perspectives of Protein Kinase C", Science, vol. 233, Jul. 18, 1986, pp. 305-312.
A. Dahlqvist et al., "Phospholipid:diacylglycerol acyltransferase: An Enzyme that Catalyzes the acyl-CoA-independent Formation of Triacylglycerol in Yeast and Plants", PNAS, Jun. 6, 2000, vol. 97, No. 12, pp. 6487-6492.
P. Oelkers et al., "A Lecithin Cholesterol Acyltransferase-like Gene Mediates Diacylglycerol Esterification in Yeast", The Journal of Biological Chemistry, vol. 275, No. 21, May 2000, pp. 15609-15612.
C. Somerville et al., "Plant Lipids: Metabolism, Mutants, and Membranes", Science, vol. 252, Apr. 5, 1991, pp. 80-87.
E. Zinser et al., "Phospholipid Synthesis and Lipid Composition of Subcellular Membranes in the Unicellular Eukaryote *Saccharomyces cerevisiae*" Journal of Bacteriology, Mar. 1991, pp. 2026-2034.
N. Green et al., Immunogenic Structure of the Influenza Virus Hemagglutinin, Cell, vol. 28, Mar. 1982, pp. 477-487.
E. Engvall, Enzyme Immunoassay ELISA and EMIT, Methods in Enzymology, vol. 70, pp. 419-439.
H. Towbin et al., "Electrophoretic Transfer of Proteins from Polyacrylamide Gels to Nitrocellulose Sheets: Procedure and Some Applications", Proc. Natl. Acad. Sci. USA, vol. 76, No. 9, Sep. 1979, pp. 4350-4354.
S. Wakil et al., "Fatty Acid Synthesis and Its Regulation", Ann. Rev. Biochem. 1983, 52, pp. 537-579.
C. O. Rock et al., "Improved Purification of Acyl Carrier Protein,"Analytical Biochemistry 102, 1980, pp. 362-364.

* cited by examiner

*Primary Examiner*—Nancy Vogel
(74) *Attorney, Agent, or Firm*—Oliff & Berridge, PLC

(57) ABSTRACT

This invention describes novel catalytically active cytosolic enzymes for triacylglycerol biosynthesis from eukaryotic systems. The complex from oleaginous yeast was enzymatically characterized, and was found to contain lysophosphatidic acid acyltransferase, phosphatidic acid phosphatase, diacylglycerol acyltransferase, acyl—acyl carrier protein synthetase, superoxide dismutase and acyl carrier protein. The triacylglycerol biosynthetic machinery rapidly incorporates free fatty acids as well as fatty acyl-coenzyme A into triacylglycerol and its biosynthetic intermediates. Lysophosphatidic acid acyltransferase, phosphatidic acid phosphatase and diacylglycerol acyltransferase from the complex were microsequenced. Acyl carrier protein, superoxide dismutase and diacylglycerol acyltransferase genes were cloned and expressed in bacterial system. The soluble triacylglycerol biosynthetic enzymes (lysophosphatidic acid acyltransferase, phosphatidic acid phosphatase, diacylglycerol acyltransferase) in yeast, rat adipocytes and human hepatocyte cell-line (HepG2) exist in the cytosol either as free enzymes or as a multienzyme complex.

2 Claims, 16 Drawing Sheets

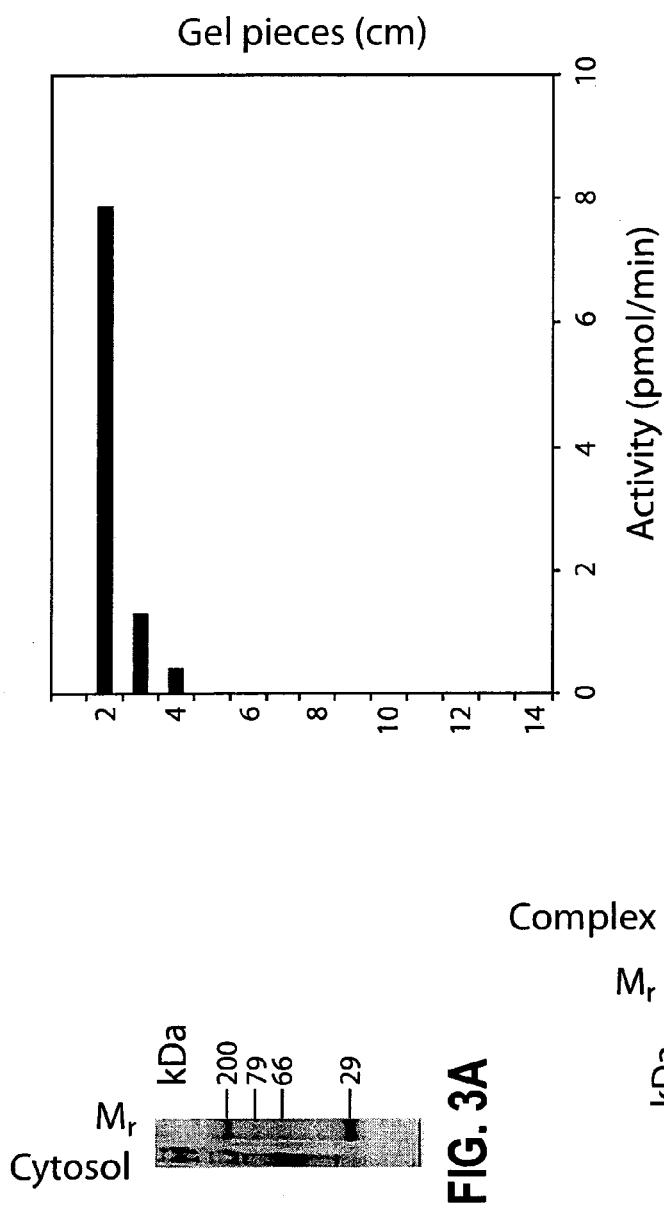

```
GGCACCAGGGGCGACGACTCGAGCCATGGCCGCCTATAACAAGATCCCTGCTGTTCTCCC                    60
                  M  A  A  Y  N  K  I  P  A  V  L  P                           12
GAAGCTTCCCTTCGCGTACAACGCTCTGGAGCCGGCCATTCCTCCCAGATCATGGAGCT                    120
 K  L  P  F  A  Y  N  A  L  E  P  A  I  S  S  Q  I  M  E  L                    32
CCACCACTCGAAGCACCACCGCCAGGAGCACCTACGTCGCCAACTTCAACAAGGCCACGAGGACAT             180
 H  H  S  K  H  H  A  T  Y  V  A  N  F  N  K  A  H  E  D  I                    52
CCAGGCTGCTTCGCAGGACATCAAGAAGCAGATTGCCCTCCAGGCCACCGTCAA                         240
 Q  A  A  S  Q  A  Q  D  I  K  K  Q  I  A  L  Q  A  T  V  K                    72
GTTCAACGGCGGTGGCCACATCAACCACCCTCTTCTGGGAGAACCTCGCCCCCAGTC                      300
 F  N  G  G  G  H  I  N  H  T  L  F  W  E  N  L  A  P  Q  S                    92
GCAGGGGCGGCCAGTTCCCCTCGTCGAAGCTTCATGACCAAGTCCAGCAGGACTT                        360
 G  G  G  Q  F  P  S  S  K  L  H  D  Q  V  Q  Q  D  F                          112
CGGGCGGTCTCGACGGCTTTGAAGAAGGCCGTCAACGCCGCTGCCCGTATCCAGGGAT                     420
 G  G  L  D  G  F  E  E  G  R  Q  R  R  C  P  R  Y  P  G  I                    132
CTGGATGGGCCTGGCCCGGGTACAACCCGACGAACAACCTTGAGGCTGTCTCGACC                       480
 W  M  G  L  A  R  G  T  T  R  R  P  R  T  L  R  L  S  R  P                    152
GCAACCAGGAGGCCACTTCTTCCCCGTACGTTCCCGGACATGTGGGAGCAC                            540
 Q  P  G  T  R  F  S  A  T  F  P  P  S  A  W  T  C  G  S  T                    172
GCTTACTACATCGACTACAAGAAGTCAAGGCCTCGTACCTCGAAGTCTCTCGAGGCCTA                    600
 L  T  T  S  T  T  R  S  Q  G  L  V  P  R  S  L  S  E  A  *                    191
AGTCTCGCCCTTCCCTTCTCGAGCCCGCTTGGAAGGAAGGAAGGAATGCGCTTGAA                       660
CCCATGTAGTACGCGAAAAGTCGAAATACGAAATCCCCTCAGTCGTTGCAAAAAAAAAA                    720
AAAAAAAAAA                                                                    732
```

```
human       MLSRAVCGTSRQLAPALG------------------YLGSRQKHS PDLPYDYGALEP HINAQI  46
bovine      MLSRAACSTSRRLVPALS------------------VLGSRQKHS PDLPYDYGALEP HINAQI  46
rabbit      ---------------------------------------HGRGMKHS PDLPYDYGALEP HINAQI  27
rat         MLCRAACSAGRRLGPAAS------------------TAGSRHKHS PDLPYDYGALEP HINAQI  46
E.coli      -----------------------------------------MSFE PALPYAKDALAP HISAET  23
pea         MAARTLLCRKTLSSVLRNDAKPIGAAIAAASTQSRGLHVFT PDLAYDYGALEP VISGEI  60
capsicum    MALRNLMTKKPFAGILT-----------------------FRQQLRCVQTFS PDLSYDYGALEP AISGEI  48
maize       MALRTLASKKVLSFPFGG-----------------AGRPLAAAASARGVTTVT PDLSYDFGALEP AISGEI  55
microsporum -------------------------------------------MAHV PDLPYAYNALEP FISQQI  23
S.cer       MFAKTAAANLTKKGGLS-----------------------LLSTTARRTKVT PDLKWDFGALEP YISGQI  48
R.glu       ---------------------------------------MAAYNKIPAV PKLPFAYNALEP AISSQI  29
                                                          **  *  *       *

I human       MQLHHS KHHAAYVNNL NVTEEKYQEALAKGDVTA---------QIALQPALKFNGGGHINHS   99
bovine      MQLHHS KHHAAYVNNL NVAEEKYREALEKGDVTA---------QIALQPALKFNGGGHINHS   99
rabbit      MELHHS KHHAAYVNNL NATEEKYREALARGDVTA---------HVALQPALKFGGGHINHT   80
rat         MQLHHS KHHATYVNNL NVTEEKYHEALAKGDVTT---------QVALQPALKFNGGGHINHS   99
E.coli      IEYHYG KHHQTYVTNLNN-LIKGTAFEGKSLEEI---------IRSSEGGVNNAAQVWNHT   75
pea         MQIHHQ KHHQTYITNYNKALEQLHDAVAKADTST---------TVKLQNAIKFNGGGHINHS  113
capsicum    MQLHHQ KHHQTYITNYNNALQQLHDAINKGDSPT---------VAKLQGAIKFNGGGHINHS  101
maize       MRLHHQ KHHATYVANYNKALEQETAVSKGDASA---------VVQLQAAIKFNGGGHVNHS  108
microsporum MELHHK KHHQTYVNSLNAAEQAYAKASTPKER---------IALQSALKFNGGGHINHS   73
S.cer       NELHYT KHHQTYVNGFNTAVDQFQELSDLLAKEPSPANARKMIAIQQNIKFHGGGFTNHC  108
R.glu       MELHHS KHHATYVANFNKAHEDIQAASQAQDIKK---------QIALQATVKFNGGGHINHT   82
             *  *  ***                                              **
                      II
```

FIG. 7B

```
human        IFWTNLSPN--------GGGEPKGELLEAIKRDFGSFDKFKEKLTAASVGVQGSGWGWLGF 152
bovine       IFWTNLSPN--------GGGEPQGELLEAIKRDFGSFDKFKEKLTAVSVGVQGSGWGWLGF 152
rabbit       IFWTNLSPN--------GGGEPKGELLEAIKRDFGSFAKFKEKLTAVSVGVQGSGWGWLGF 133
rat          IFWTNLSPK--------GGGEPKGELLEAIKRDFGSFEKFKEKLTAVSVGVQGSGWGWLGF 152
E.coli       FYWNCLAPN--------AGGEPTGKVAEAIAASFGSFADFKAQFTDAAIKNFGSGWTWLVK 128
pea          IFWKNLAPVSE------GGGEPPKESLGWAIDTNFGSLEALIQKINAEGAALQ-----WLGL 164
capsicum     VFWKNLAPTRE------GGGEPPKGSLGSAIDTNFGSLEAVIQKMNAEGAALQGSGWVLGL 157
maize        IFWKNLKPISE------GGGEPPHGKLGWAIDEDFGSFEALVKKMNAEGAALQGSGWVLAL 164
microsporum  LFWKNLAPAKSEGKGNGGALADGPLKSAIEQNWGSVDNFIKEFNATTAAIQGSGWGWLGL 133
S.cer        LFWENLAPESQ------GGGEPPTGALAKAIDEQFGSLDELIKLTNTKLAGVQGSGWAFIVK 164
R.glutinis   LFWENLAPQSQ------GGGQFPSSGKLHDQVQQDFGGLDGFEEGRQRRCPRYPG---IWMGL 136
             .:* * *                                                ::

human        NKER-GHLQIAACPNQDPLQG-TTGLIPLLGIDVWEHAYYLQYKNVRPDYLKAIWNVINW 210
bovine       NKEQ-GRLQIAACSNQDPLQG-TTGLIPLLGIDVWEHAYYLQYKNVRPDYLKAIWNVINW 210
rabbit       NKEQ-GHLQIAACANQDPLQG-TTGLIPLLGIDVWEHAYYLQYKNVRPDYLKAIWNVITW 191
rat          NKEQ-GRLQIAACSNQDPLQG-TTGLIPLLGIDVWEHAYYLQYKNVRPDYLKAIWNVINW 210
E.coli       NSD--GKLAIVSTSNAG-TPL-TTDATPLLTVDVWEHAYYIDYRNARPGYLEHFWALVNW 184
pea          DRDL-KRLVVET--TQDPLVTKGASLVPLLGIDVWEHAYYLQYKNVRPDYLKNIWKVINW 221
capsicum     DKEL-KRLVIETTANQDPLVIKGPNLVPLLGIDVWEHAYYLQYKNVKPDYLKNIWKVINW 216
maize        DKEA-KKVSVETTANQDPLVTKGASLVPLLGIDVWEHAYYLQYKNVRPDYLKNIWKVMNW 223
microsporum  NPAT-KRLEITTANQDPLLS----HVPIIGVDIWEHAFYLQYLNVKADYLNNIWKVINF 188
S.cer        NLSNGGKLDVVQTYNQDTVTG---PLVPLVAIDAWEHAYYLQYQNKKADYFKAIWNVVNW 221
R.glutinis   ARGTTRRPRTLRLSRPQPGTR----FSATEPRSALTCGSTLTTSTTR--------S-Q 181
                                   ::                            :
```

III

| | | |
|---|---|---|
| human | ENVTERYMACKK | 222 |
| bovine | ENVTARYTACSK | 222 |
| rabbit | ENVTERYMACK- | 202 |
| rat | ENVSQRYIVCKK | 222 |
| *E.coli* | EFVAKNLAA--- | 193 |
| pea | KHASEVYEKESS | 233 |
| capsicum | KYAAEVYEKECP | 228 |
| maize | KYAGEVYENVLA | 235 |
| microsporum | KEAERRLIEATK | 200 |
| S.cer | KEASRRFDAGKI | 233 |
| *R.glutinis* | GLVPRSLSEA-- | 191 |

FIG. 7C

```
GGCACGAGGCTCTCACATGTTGCCGCTACATTTCAGCTTAAAGGGTCTATTCAGCT        60
CACGATGAAGCACGTCGCCGCCTACCTCCTCGTCTCTGCCGGCAACACCTCGCCCTC      120
  M  K  H  V  A  A  Y  L  L  L  V  S  A  G  N  T  S  P  S       19
GGCCGAGGACGTCAAGAAGGTCCTCGCCGCCGACATCCAGGCCGACGAGGAGCGCCT      180
 A  E  D  V  K  K  V  L  A  A  D  I  Q  A  D  E  E  R  L        39
CTCGGTCCTCATCAAGGAGCTCGAGGGCAAGGACGTCAACGAGGTCATTGCCGAGGGATC   240
 S  V  L  I  K  E  L  E  G  K  D  V  N  E  V  I  A  E  G  S     59
CAAGAAGCTCGCTTCCGTCCCCTCGGGGGCCGCCCCCGCTGCCGCTGGGGGCGC         300
  K  K  L  A  S  V  P  S  G  G  A  P  A  A  A  A  G  G  A       79
TGCCGGCTGGGGGTGCCGCCGAGGAGAAGGCTGAGGACAAGCCCGCTGAGAAGGATGAGGA  360
 A  G  G  A  A  E  E  K  A  E  D  K  P  A  E  K  D  E  E        99
GAGCGACGACGACATGGGCTTCGGTCTCTTCGACTAAGCTCTTCGCCCTCTCCCCCT      420
 S  D  D  D  M  G  F  G  L  F  D  *                            109
CTGGCGACGACGCACAACTTTCCCGACCTTCCTGACTTGCCGAAGCCGTTTCATCTCTGTA  480
GTTTGGGATCGATGATGCGCTAGGGAAGCCCCTGACGGAAGAAAAGGGGGGTGGTTTGGCT  540
TCTCAAAAAAAAAAAAAAAAAAAA
```

FIG. 8

| | | |
|---|---|---|
|Cladosporium|MKYMAAYLLLGLAGNSSPSPSAEDIKTVLSSVGIDADEERLSSLLKELEGKDINELISSGSQ|60|
|Alternata|MKHLAAYLLLGLGGNTSPSAADVKAVLESVGIEADSDRLDKLISELEGKDINELIASGSE|60|
|R.|MKHVAAYLLLVSAGNTSPSAEDVKKVLAAADIQADEERLSVLIKELEGKDVNEVIAEGSK|60|
|S.|MKYLAAYLLLTVGGKDSPSASDIESVLSTVGIEAESERIETLINELNGKDIDELIAAGNE|60|
|maize|MKVIAAYLLAVLGGNTSPTADDVKSILESVGAEADEEKLEFLLTELKDKITEVIAAGRE|60|
|rat|MRYVASYLLAALGGNSNPSAKDIKKILDSVGIEADDERLNKVISELNGKNIEDVIAQGVG|60|
|human|MRYVASYLLAALGGNSSPSAKDIKKILDSVGIEADDDRLNKVISELNGKNIEDVIAQGIG|60|
| |*:  :.****   .*:  .*:: *: ..  :.:*:: ::.:***.:*::  ::: :|*|

| | | |
|---|---|---|
|Cladosporium|KLASVPSGGSGAAPSAGGAAAAGG--ATEAAPEAAKEEEKEE---SDDDMGFGLFD|111|
|Alternata|KLASVPSGGAGGAAASGGAAAAGGSAQAEAAPEAAKEEEKEE---SDEDMGFGLFD|113|
|R.|KLASVPSGGAAPAAAGG--AAAGG--AAEEKAEDKPAEKDEE---SDDDMGFGLFD|110|
|S.|KLATVPTGG---AASAAPAAAAGG--AAPAAEEAAKEEEKEEEE-SDEDMGFGLFD|110|
|maize|RLSSVPSGGGAIDMGAPAAVAGGGAAPAEEAKKEEKVEEKEE---SDEDMGFSLFD|113|
|rat|KLASVPAGGAVAVSAAPGSAAPAAG-SAPAAAEEKKDEKKEESEESDDDMGFGLFD|115|
|human|KLASVPAGGAVAVSAAPGSAAPAAG-SAPAAAEEKKDEKKEESEESDDDMGFGLFD|115|
| |:::**    :  . ::  .   *  .  :.  .:  .:.*|

FIG. 9A

```
pylori      ------------------------------------------------MALFED-IQAVIAEQ  14
plasmodium  MFVVLSYVYGVSLQILKKKRSNQVNFLNRKNDYNLIRKNPSSSLKSTFDD-IKKIISKQ    59
pseudomonas ------------------------------------------------MSTIEERVKKIVAEQ  15
e.coli      ------------------------------------------------MSTIEERVKKIIGEQ  15
s.cer       MFRSVCRISSRVAPSAYRTIMGRSVMSNTILAQRFYSANLSRDQVSQRVIDVIKAFDKNS     60
brassica    ------------------------------------------------NLSFNLGRSIPTR    13
rglutinis   -----------MKHVAAYLLLVSAGNTSPSAEDVKKVLAAADIQADERLSVLIKELEGKD    49
                                                                  :  .  .:

pylori      LNVDAAQVTPEAEFVKDLGADSLDVVELIMALEEKFNIEIPDEQAEKIVNVGDVVKYIED     74
plasmodium  LSVEEDKIQMNSNFTKDLGADSLDLVELIMALEEKFNVTISDQDALKINTVQDAIDYIEK    119
pseudomonas LGVKEEEVTNSASFVEDLGADSLDTVELVMALEEEFETEIPDEKAEKITTVQEAIDYIVA    75
e.coli      LGVKQEEVTNNASFVEDLGADSLDTVELVMALEEEFDTEIPDEEAEKITTVQAAIDYING   75
s.cer       PNIANKQISSDTQFHKDLGLDSLDTVELLVAIEEEFDIEIPDKVADELRSVGETVDYIAS   120
brassica    LSVS----CAAKPETIEKVS----KIVKKQLSLKDD-QKVVAETKFADLG--ADSLDTV--  61
rglutinis   VNEVIAEGSKKLASVPSGGAAPAAAAG-GAAAGGAAEEKAEDKPAEKDEESDDDMGFGLF  108
                .     .    .          . .       .          .  .

pylori      NKLA-  78
plasmodium  NNKQ- 123
pseudomonas HQQ--  78
e.coli      HQA--  78
s.cer       NPDAN 125
brassica    -----
rglutinis   D---- 109
```

FIG. 9B

*Rhodoturula glutinis* soluble DAGAT sequence:

```
ACACTAGTGGATCCAAAGAATTCGGCACGAGGCTCGGCTCTCTCGCGTCTTTACGTCCCG
        T  L  V  D  P  K  N  S  A  R  G  S  A  L  S  R  L  Y  V  P
AAGGGTCTGTGGGAGGGCGAGGGCAAGTTCAAGGAGATCCTTCTCTCCGAGGTTGCCAAG
 K  G  L  W  E  G  E  G  K  F  K  E  I  L  L  S  E  V  A  K
ATCACTCTCGGCCCCGTCACCGAGTTCGAGCACTTCATGGGTCCCGTCATCTCGCAGGCT
 I  T  L  G  P  V  T  E  F  E  H  F  M  G  P  V  I  S  Q  A
TCGTTCGACAAGTGCCTCAGCTACGTTGAGAAGGCCAAGCAGGCAGGTGGCGAGGTCCTC
 S  F  D  K  C  L  S  Y  V  E  K  A  K  Q  A  G  G  E  V  L
GCCGGCGGCAAGGGCGACGCGTCGAGCGGTTACTACGTCGAGCCGACCATCATCCTGACC
 A  G  G  K  G  D  A  S  S  G  Y  Y  V  E  P  T  I  I  L  T
AAGGACCCTCGCTCGCCTACCATGGTCGACGAGATCTTCGGCCCGGTCCTCACTGTTTAC
 K  D  P  R  S  P  T  M  V  D  E  I  F  G  P  V  L  T  V  Y
ATCTTCGAGGACGACCAGTACGAGGAGACGTGCAAGTTGATCGACCAGACGACGACGTAC
 I  F  E  D  D  Q  Y  E  E  T  C  K  L  I  D  Q  T  T  T  Y
GCCCTCACTGGCTGCATCTTCTCGGACGACCGTGCCGCGACTGTCAAGGCCGGTGCTCTC
 A  L  T  G  C  I  F  S  D  D  R  A  A  T  V  K  A  G  A  L
CTCCGCCACGCTGCGGGTAACTACTACATCAACGACAAGTCGACCGGTGCTGTTGTCGGT
 L  R  H  A  A  G  N  Y  Y  I  N  D  K  S  T  G  A  V  V  G
GCCCAGCCTTTCGGTGGCGCACGCGGATCGGGCACGAACGACAAGGCGGGCTCGATGACG
 A  Q  P  F  G  G  A  R  G  S  G  T  N  D  K  A  G  S  M  T
TTCTTCACCCGCTGGTGCCAGCCGCGGAGTGTGAAGGAATCCTTCTGCCCGCCCGAATCT
 F  F  T  R  W  C  Q  P  R  S  V
TTCCCTTACCCGTCGAACCAGCGCGATTAAATGGAGGAGTTGGGGAGGAGGAGGACGTCG
AGGGAGCTGGGGAGGCGGAGGACGTCGAGGAGGAGTTGGGGAGGAGGAGGACGTCGAGGG
AGCTGGGGAGGCGGAGGACGTCGAGGAGGAGTTGGGGAGGAGTTTGTCGAGGAGGAGGAG
AAGGGTTTCTCCTCGCCTGTAGTTGTACAAAATCAGCACGCCTTTGCTTCCACCGCCAAA
AAAAAAAAAAAAAAAAAAACTCGAGAGTACTTCTAGAGCGGCCGCGGGCCCATCGATTTTC
CACCCGGGTGGGGTACCAGGTAAGTGTACCCAATTCGCCCTATAGTGAGTCGTATTACAA
TTCACTGGCCGTCGTTTTACAACGTCGTGACTGGGAAAACCCTGGCGTTACCCAACTTAA
       TCGCCTTGCAGCACATCCCCCTTTCGCCAGCTGGCGTAATAGCGAAGAGGCCCGGACCGA
TCGCCCTTCCAACAGTTGCGCAGCCTGATGGCGAATGGAGATCCAATTTTTAAGTGTATA
AGGGGTAAACTACTGATCTAATTGTGGGGTTTTTAAAT
```

FIG. 10

TRIACYLGLYCEROL BIOSYNTHESIS IN THE CYTOSOL OF EUKARYOTES

TECHNICAL FIELD

This invention relates to novel catalytically active cytosolic enzymes for triacylglycerol biosynthesis from eukaryotic systems. The complex from oleaginous yeast was enzymatically characterized and was found to contain lysophosphatidic acid acyltransferase, phosphatidic acid phosphatase, diacylglycerol acyltransferase, acyl—acyl carrier protein synthetase, superoxide dismutase and acyl carrier protein. The triacylglycerol biosynthetic machinery rapidly incorporates free fatty acids as well as fatty acyl-coenzyme A into triacylglycerol and its biosynthetic intermediates. Lysophosphatidic acid acyltransferase, phosphatidic acid phosphatase and diacylglycerol acyltransferase from the complex were microsequenced. Acyl carrier protein, superoxide dismutase and diacylglycerol acyltransferase genes were cloned and expressed in bacterial system. The triacylglycerol biosynthetic enzymes such as lysophosphatidic acid acyltransferase, phosphatidic acid phosphatase and diacylglycerol acyltransferase in baker's yeast, rat adipocytes and human hepatocyte cell-line can exist in the cytosol as free enzymes.

BACKGROUND ART

The de novo biosynthesis of triacylglycerol has been shown to occur by the sequential acylation of glycerol-3-phosphate (1–3). Glycerol-3-phosphate acyltransferase catalyzes the first step in glycerolipid synthesis (4) generating lysophosphatidic acid (LPA). Alternatively, LPA is formed by acylation followed by reduction of dihydroxyacetone phosphate that are catalyzed by dihydroxyacetone phosphate acyltransferase (5) and acyl-dihydroxyacetone phosphate reductase (6, 7), respectively. The acylation of LPA is catalyzed by LPA acyltransferase to form phosphatidic acid (PA), which is a branch point for the synthesis of diacylglycerol (DAG) and phospholipids. PA phosphatase catalyzes the dephosphorylation of PA to DAG that is an immediate precursor for triacylglycerol (TAG), phosphatidylcholine and phosphatidylethanolamine. DAG can also be derived from phospholipids by the action of phospholipase C (8), which is an important signal molecule that activates protein kinase C (9). DAG acyltransferase catalyzes the acylation of DAG, which is the committed step in TAG biosynthesis. Recently, it has been shown in plants and yeast cells that an acyl-CoA independent enzyme for TAG synthesis that uses phospholipid as acyl donor and DAG as acyl acceptor. This reaction is catalyzed by phospholipid:DAG acyltransferase (10). The same reaction is also catalyzed by lecithin:cholesterol acyltransferase (11). All the enzymes in these pathways are shown to be membrane-bound in eukaryotic systems (1–4, 12, 13). Both mitochondrial membranes and endoplasmic reticulum (ER) have been identified as the major sites for phospholipid and TAG synthesis in *S. cerevisiae* (3, 6, 14).

A number of fungi are known to have high levels of TAG. Understanding the lipid biosynthesis would enable to genetically engineer fungi and plants with desired fatty acid composition and the altered oil content (15).

While there is no direct evidence to support the possibility that membranes are the only sites for TAG synthesis, there is also no evidence for the absence of this biosynthetic pathway in the cytosol. The presence of soluble enzymes that provide important precursors for triacylglycerol biosynthesis is well documented.

TAG enzymes in yeast comprise of lysophosphatidic acid acyltransferase, phosphatidic acid phosphatase, diacylglycerol acyltransferase, acyl—acyl carrier protein synthetase and acyl carrier protein. These TAG biosynthetic enzymes may exist as either free or multienzyme complex. Among these enzymes, lysophosphatidic acid acyltransferase can be identified in any yeast strain by immunological cross reactivity to the peptide sequence ALELQADDFNK (peptide SEQ ID NO: 2), diacylglycerol acyltransferase identified by immunological cross reactivity to the peptide sequence XLWAVVGAQPFGGARGS (peptide SEQ ID NO: 7) and phosphatidic acid phosphatase identified by immunological cross reactivity to peptides NALTGLHMGGGK (peptide SEQ ID NO: 4) and YVEGARP (peptide SEQ ID NO: 6). TAG biosynthetic enzymes thus isolated from oleaginous yeast can utilize free fatty acids or fatty acyl-CoA or acyl-ACP as substrates.

In oleaginous yeasts and other lipid rich fungi, biochemical and genetic study of these enzyme systems would enable to genetically engineer fungi and plants with desired fatty acid composition and altered oil content. Using modern methods of genetics, these enzymes may be produced by recombinant gene expression; the recombinant proteins may be reconstituted to active TAG biosynthetic complex; the complex may be suitably assayed to identify specific inhibitors of TAG biosynthesis, which may have a potential value as lipid lowering drugs in humans.

Keeping with and to further studies conducted, Applicant investigated cytosolic TAG biosynthetic pathway using *Rhodotorula glutinis* and other *Saccharomyces cerevisiae*, rat adipocytes and human hepatocytes cell-line.

SUMMARY

The main object of the present invention is to determine the source of the biosynthetic pathway in yeasts. Another object is to isolate TAG biosynthetic enzymes using yeast species. Yet another object is to identify and isolate novel TAG biosynthetic enzymes in yeast. Still another object is to identify the gene sequences encoding TAG biosynthetic enzymes. Another object is to develop an assay for the isolation of cytosolic TAG biosynthetic enzymes from yeast using free fatty acids or fatty acyl CoA or Acyl ACP as substrates. Another object is to demonstrate the cytosolic TAG biosynthetic enzymes from *Saccharomyces cerevisiae*, rat adipocytes and human hepatocytes cell-line.

In accordance with the above objects, the invention provides a novel source for isolation of TAG enzymes. The invention also provides novel TAG biosynthetic enzymes in yeast and gene sequences and gene sequences encoding these enzymes. The invention is described in detail herebelow with reference to the examples, which should not be construed as limitations on the inventive concept herein.

This invention provides the identification of soluble triacylglycerol biosynthetic machinery in yeasts, rat adipocytes (white and brown), human hepatocytes (HepG2 cell line), which are involved in triacylglycerol biosynthesis.

Thus, the invention provides novel soluble triacylglycerol (TAG) biosynthetic enzymes in eukaryotic cells. These soluble TAG enzymes are soluble in water and detergent solutions.

In the invention, the soluble TAG enzymes in yeast comprise lysophosphatidic acid acyltransferase with peptide SEQ ID NO: 1 XALELQADDFNK and peptide SEQ ID NO: 3 XXVNNVXPGXIEQ, phosphatidic acid phosphatase with peptide SEQ ID NO: 4 NALTGLHMGGGK and peptide SEQ ID NO: 5 YVEGARPXK, diacylglycerol acyltransferase with peptide SEQ ID NO: 7 XLWAVVGAQPFGGARGS, acyl—acyl carrier protein synthetase with peptide SEQ ID NO: 8 VHLAVALYGLAAVRVSRIVR, superoxide dismutase encoded by the gene sequence as in SEQ ID NO: 9, and acyl carrier protein encoded by the gene sequence as in SEQ ID NO: 10. The gene sequence encoding superoxide dismutase and diacylglycerol acyltransferase acyl carrier protein have sequence homology to DNA sequences as in SEQ ID NO: 9, SEQ ID NO: 11 and SEQ ID NO: 10, respectively. The lysophatidic acid acyltransferase is identified by immunological cross reactivity to the peptide sequence ALELQADDFNK (as in peptide SEQ ID NO: 2), diacylglycerol acyltransferase is identified by immunological cross reactivity to the peptide sequence XLWAVVGAQPFGGARGS (as in peptide SEQ ID NO: 7) and phosphatidic acid phosphatase is identified by immunological cross reactivity to peptides NALTGLHMGGGK (as in peptide SEQ ID NO: 4) and YVEGARP (as in peptide SEQ ID NO: 6).

The enzymes responsible for TAG synthesis and accumulation are either in free or multi enzyme complex form.

The novel soluble TAG biosynthetic enzymes can be used to identify compounds that are capable of altering for TAG synthesis and accumulation.

This invention provides method for isolation of soluble triacylglycerol biosynthetic machinery from eukaryotes, which are responsible for triacylglycerol biosynthesis. The eukaryotic cells are selected from yeast, rat adipocytes and human cell-lines (HepG2).

This invention provides the soluble triacylglycerol biosynthetic machinery from oleaginous yeast, which are responsible for triacylglycerol accumulation.

This invention provides a method of obtaining a polypeptide(s) in purified form which comprises: (a) introducing the vector comprising the isolated nucleic acid which encodes a superoxide dismutase (SOD) (SEQ ID NO: 9) and acyl carrier protein (ACP) (SEQ ID NO: 10) and diacylglycerol acyltransferase (SEQ ID NO: 11) into a suitable host cell; (b) culturing the resulting cell so as to produce the polypeptide; (c) recovering the polypeptide produced in step (b); and (d) purifying the polypeptide so recovered.

This invention provides purified polypeptides, which are lysophosphatidic acid acyltransferase, phosphatidic acid phosphatase, diacylglycerol acyltransferase, acyl carrier protein, acyl-ACP synthetase and superoxide dismutase.

This invention provides an oligopeptide of at least 5 to 20 amino acids (peptide SEQ ID NOs: 1 to 8) capable of specifically identifying with a unique sequence of proteins present within a triacylglycerol biosynthetic complex (TBC).

This invention provides antibodies to an at least 5 to 20 amino acids (peptide SEQ ID NOs: 1 to 8) from the isolated polypeptides from TBC, which are capable of specifically identifying the proteins present within a triacylglycerol biosynthetic complex.

This invention provides an oligonucleotide of at least 15 nucleotides from SEQ ID NO: 9 capable of specifically hybridizing with a unique sequence of nucleotides present within a nucleic acid, which encodes a superoxide dismutase (SOD).

This invention provides an oligonucleotide of at least 15 nucleotides from SEQ ID NO: 10 capable of specifically hybridizing with a unique sequence of nucleotides present within a nucleic acid, which encodes an acyl carrier protein (ACP).

This invention provides a nucleic acid having a sequence complementary to the sequences (SEQ ID NOs: 9 to 11) of the isolated nucleic acid, which encode superoxide dismutase and acyl carrier protein and diacylglycerol acyltransferase.

This invention provides an in vitro method of detecting the soluble triacylglycerol biosynthetic enzymes, which exist either as free or as complex in the cytosol.

This invention provides a method for determining whether a subject known to have an imbalance in triacylglycerol has the imbalance due to a defect in the synthesis of triacylglycerol.

This invention provides a method for treating a subject who has an imbalance in triglyceride (triacylglycerol) levels due to a defect in the synthesis of soluble triglyceride, which comprises introducing the isolated nucleic acid which encodes lysophosphatidic acid acyltransferase, phosphatidic acid phosphatase, diacylglycerol acyltransferase, acyl carrier protein (ACP), acyl-ACP synthetase and superoxide dismutase into the subject under conditions such that the nucleic acid expresses the soluble triacylglycerol biosynthetic enzymes individually or in combination, so as to thereby treat the subject.

This invention provides a method for inhibiting the soluble triacylglycerol biosynthetic enzymes in a subject which comprises transforming appropriate cells from the subject with a vector which expresses the nucleic acid which encodes the components in TBC, and introducing the transformed cells into the subject so as to thereby inhibit the soluble enzyme and/or complex.

This invention provides a method for inhibiting the soluble triacylglycerol biosynthetic enzymes in a subject which comprises introducing the any of the above-described oligonucleotides of at least 15 nucleotides capable of specifically hybridizing with a unique sequence of nucleotides present within a nucleic acid which encode lysophosphatidic acid acyltransferase, phosphatidic acid phosphatase, diacylglycerol acyltransferase, acyl carrier protein (ACP), acyl-ACP synthetase and superoxide dismutase into the subject so as to thereby inhibit the triglyceride formation and accumulation.

This invention provides a method for identifying a chemical compound which is capable of inhibiting soluble triacylglycerol biosynthetic enzyme(s) in a subject which comprises: (a) contacting soluble triacylglycerol biosynthetic enzyme(s) with chemical compound under conditions permitting binding between the soluble triacylglycerol biosynthetic enzyme(s) and the chemical compound; (b) detecting specific binding of the chemical compound to the soluble triacylglycerol biosynthetic enzyme(s); and c) determining whether the chemical compound inhibits the activity of the soluble triacylglycerol biosynthetic enzyme(s) so as to identify a chemical compound which is capable of inhibiting soluble triacylglycerol biosynthetic enzyme(s) in a subject.

This invention provides a method for identifying a chemical compound which is capable of enhancing soluble triacylglycerol biosynthetic enzyme(s) in a subject which comprises: (a) contacting the soluble triacylglycerol biosynthetic enzyme(s) with the chemical compound under conditions permitting binding between the soluble triacylglycerol biosynthetic enzyme(s) and the chemical compound; (b) detecting specific binding of the chemical compound to the soluble triacylglycerol biosynthetic enzyme(s); and c) determining whether the chemical compound enhances the activity of the soluble triacylglycerol biosynthetic enzyme(s) so as to identify a chemical compound which is capable of enhancing soluble triacylglycerol biosynthetic enzyme(s) in a subject.

This invention provides a pharmaceutical composition comprising the chemical compound(s), which is capable of inhibiting soluble triacylglycerol biosynthetic enzyme(s) identified by the above-described method in an amount effective to inhibit soluble triacylglycerol biosynthetic enzyme(s) in a subject and a pharmaceutically effective carrier.

This invention provides a pharmaceutical composition comprising the chemical compound, which is capable of enhancing soluble triacylglycerol biosynthetic enzyme(s) activity identified by the above-described method in an amount effective to enhance soluble triacylglycerol biosynthetic enzyme(s) activity in the subject and a pharmaceutically effective carrier.

This invention provides a method of treating a subject who has atherosclerosis comprising the pharmaceutical composition comprising the chemical compound which is capable of inhibiting soluble triacylglycerol biosynthetic enzyme(s) identified by the above-described method in an amount effective to inhibit soluble triacylglycerol biosynthetic enzyme(s) in a subject and a pharmaceutically effective carrier.

This invention provides a method of treating a subject who has hyperlipidemia comprising the pharmaceutical composition comprising the chemical compound which is capable of inhibiting soluble triacylglycerol biosynthetic enzyme(s) identified by the above-described method in an amount effective to inhibit soluble triacylglycerol biosynthetic enzyme(s) in a subject and a pharmaceutically effective carrier.

This invention provides a method of reducing the deposition of fat cells in a subject by decreasing the amount of triglycerides produced in adipose cells of the subject comprising administering the pharmaceutical composition comprising the chemical compound which is capable of inhibiting soluble triacylglycerol biosynthetic enzyme(s) identified by the above-described method in an amount effective to inhibit diacylglycerol acyltransferase in a subject and a pharmaceutically effective carrier.

This invention provides a transgenic, nonhuman mammal comprising the isolated nucleic acid, which encode lysophosphatidic acid acyltransferase, phosphatidic acid phosphatase, diacylglycerol acyltransferase, acyl carrier protein (ACP), acyl-ACP synthetase and superoxide dismutase.

This invention provides a method of obtaining soluble triacylglycerol (TAG) biosynthetic enzymes using polyacrylamide gel electrophoresis, chromatographic procedures or density gradient centrifugation, said method comprising subjecting blue sepharose, DEAE matrix octail sepharose, antibodies raised from the peptide SEQ ID NOs: 1 to 8 and identifying and isolating the complex as a whole or individual components thereof.

This invention provides antibodies directed to an epitope of a purified lysophosphatidic acid acyltransferase, phosphatidic acid phosphatase, diacylglycerol acyltransferase, acyl carrier protein, acyl-ACP synthetase and superoxide dismutase. This invention provide antibodies capable of specifically binding to a purified lysophosphatidic acid acyltransferase, phosphatidic acid phosphatase, diacylglycerol acyltransferase, acyl carrier protein, acyl-ACP synthetase and superoxide dismutase.

This invention provides a vector comprising the isolated nucleic acid which encode SOD and ACP related gene products.

This invention provides a purified lysophosphatidic acid acyltransferase, phosphatidic acid phosphatase, diacylglycerol acyltransferase, acyl carrier protein, acyl-ACP synthetase and superoxide dismutase related gene products.

This invention provides an oligonucleotide of at least 15 nucleotides capable of specifically hybridizing with a unique sequence of nucleotides present within a nucleic acid which encode lysophosphatidic acid acyltransferase, phosphatidic acid phosphatase, diacylglycerol acyltransferase, acyl carrier protein (ACP), acyl-ACP synthetase and superoxide dismutase related gene products lysophosphatidic acid acyltransferase, phosphatidic acid phosphatase, diacylglycerol acyltransferase, acyl carrier protein (ACP), acyl-ACP synthetase and superoxide dismutase.

This invention provides a nucleic acid having a sequence complementary to the sequence of the isolated nucleic acid which encode lysophosphatidic acid acyltransferase, phosphatidic acid phosphatase, diacylglycerol acyltransferase, acyl carrier protein (ACP), acyl-ACP synthetase and superoxide dismutase related gene products.

This invention provides antibodies directed to epitopes of a purified components of TBC lysophosphatidic acid acyltransferase, phosphatidic acid phosphatase, diacylglycerol acyltransferase, acyl carrier protein (ACP), acyl-ACP synthetase and superoxide dismutase related gene products. This invention provides antibodies capable of specifically binding to a purified TBC and its components related gene products.

BRIEF DESCRIPTION OF THE DRAWINGS

The invention is illustrated by the following figures wherein:

FIG. 3. (A) TAG biosynthetic enzymes exist as a complex in the cytosol Native-PAGE (7%) profile of R. glutinis cytosol. The cytosol Native-PAGE (7%) profile is indicated in lane 1. The mobility of electrophoretic markers is shown on the right (lane 2). (B) Cytosol was electrophoresed on 7% native gel and the proteins were eluted from the gel pieces. LPA acyltransferase, PA phosphatase and DAG acyltransferase activities were measured from the eluted proteins. The protein eluted from the $2^{nd}$ cm of the native gel showed highest TAG synthase activity. (C) TAG biosynthetic enzymes exist as a multienzyme complex in the cytosol. Native polyacrylamide gel-eluted active fraction was analyzed by 12% SDS-PAGE and five proteins were visualized upon silver staining (lane 2) indicating that the cytosolic TAG biosynthetic enzymes are organized in the form of a multienzyme complex. Molecular masses are shown in lane 1.

FIG. 6. Nucleotide and deduced amino acid sequence of 21 kDa polypeptide (SEQ ID NOs: 9 and 16). The nucleotide sequence of the isolated cDNA (upper line) is presented with its deduced amino acid sequence (lower line). Nucleotides are numbered (bold face) in the 5' to 3' direction and amino acids are numbered from amino terminus starting from the first methionine residue. Putative polyadenylation signal is underlined. Asterisk indicates the stop codon of the ORF. The first 20 amino acid residues (shown underlined) were matched with the N-terminal sequence obtained from the 21 kDa protein of TBC.

FIGS. 7A–C. Multiple sequence alignment of 21 kDa protein. The deduced amino acid sequence of the isolated clone was used to search the public database (Swissprot) using BLAST algorithm. The first nine significant hits were superoxide dismutase from many different organisms (*E. coli*—SEQ ID NO: 23, *S. cerevisiae*—SEQ ID NO: 28, *Ganoderma microsporum*—SEQ ID NO: 27, maize—SEQ ID NO: 26, pea—SEQ ID NO: 24, *capsicum*—SEQ ID NO: 25, human—SEQ ID NO: 19, bovine—SEQ ID NO: 20, and rabbit—SEQ ID NO: 21), and a tenth was from rat—SEQ ID NO: 22. Multiple sequence alignment was performed with these polypeptide sequences with the isolated clone (SEQ ID NO: 29) using the ClustalW algorithm. Hyphens represent gaps introduced to obtain the best alignment. Asterisk indicates the conserved residues in all sequences in the alignment, colon indicates conserved substitutions and the dot indicates semi-conserved substitutions. Three most conserved domains present among all the SODs are marked as I, II and III; among them motif I and II are present in the isolated clone but motif III is absent.

FIG. 8. Nucleotide and deduced amino acid sequence of 10 kDa ACP (SEQ ID NOs: 10 and 17) that is a part of TBC. The nucleotide sequence of isolated ACP clone (upper line) is presented with its deduced amino acid sequence (lower line). Nucleotides are numbered in the 5'-3' direction whereas amino acids are numbered from amino terminus starting from the first methionine residue (boldface). Asterisk indicates the stop codon of the ORF.

FIG. 9. Multiple sequence alignment isolated clone. (A) The conceptual translation product of the cDNA identified from TBC was used to search the swissprot database. Six polypeptides [60S ribosomal protein II from *cladosporium* (P42038) (SEQ ID NO: 30) *S. pombe* (P08094) (SEQ ID NO: 32); major allergen of *alternaria* (P42037) (SEQ ID NO: 31); rat (P02401) (SEQ ID NO: 34); human (P05387) (SEQ ID NO: 35) and maize (O24415) (SEQ ID NO: 33) ribosomal proteins], which appeared as significant hits (scoring over 60) were multiply aligned with the cloned cDNA using ClustalW. (B) Polypeptide sequences of different Acyl Carrier Proteins (ACP) [*E. coli* (SEQ ID NO: 39), *S. cerevisiae* (SEQ ID NO: 40), *H. pylori* (SEQ ID NO: 36), *plasmodium* (SEQ ID NO: 37), pseudomonas (SEQ ID NO: 38), *brassica* (SEQ ID NO: 41)] were obtained from public database (Swissprot) and were used to do a multiple sequence alignment with the isolated ACP clone (SEQ ID NO: 42) using ClustalW algorithm. On the consensus line underneath each section of the alignment, in both panel A and B, asterisk indicates identical or conserved residues in all sequences in the alignment, colon indicates conserved substitutions and dots denote semi-conserved substitutions. (C) Local alignment of the probe used to screen the cDNA for the ACP gene with the isolated cDNA sequence. The asterisk denotes the absolute match between both the sequence fragments.

FIG. 10. Partial nucleotide and deduced amino acid sequences of soluble diacylglycerol acyltransferase (DAGAT) (SEQ ID NOs: 11 and 18) that is a part of TBC. The nucleotide sequence of isolated DAGAT clone (upper line) is presented with its deduced amino acid sequence (lower line). Nucleotides are numbered in the 5'-3' direction whereas amino acids are numbered from amino terminus. The asterisk indicates the stop codon of the open reading frame (ORF).

DETAILED DESCRIPTION OF EMBODIMENTS

Figure 1A:
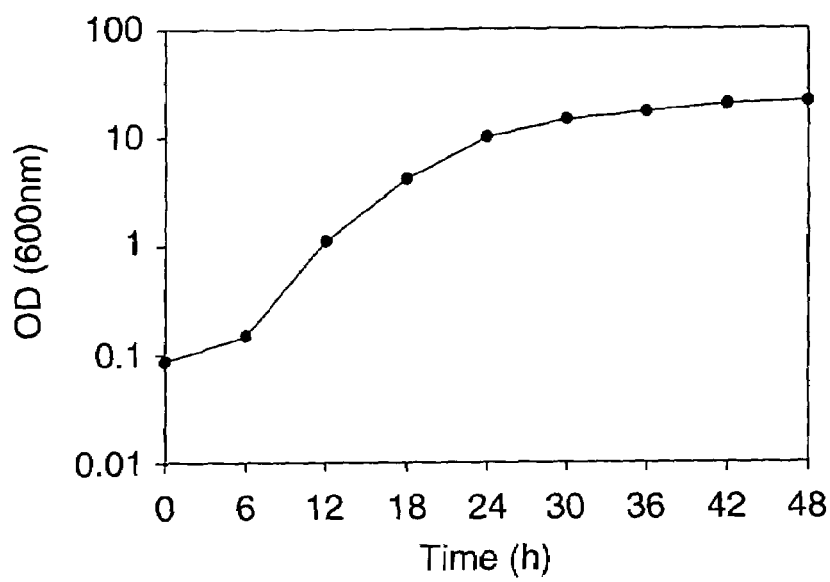
FIG. 1. (A) Growth of R. glutinis. Exponentially growing cultures of R. glutinis in malt-yeast extract medium was added to a final concentration of 1% to fresh medium and incubated at 30° C. At regular time intervals, $OD_{600\ nm}$ was measured. (B) Culture aliquots were taken at regular time intervals, diluted and the cell counts taken. Viable cells were expressed, as colony-forming units/ml. (C) TAG formation in R. glutinis. Profile of TAG accumulation in R. glutinis at the indicated time points was determined. Cells were isolated at different growth times and the cell number was adjusted to 2.0 $OD_{600\ nm}$. Lipids were extracted and separated by silica-TLC using neutral lipid solvent system. (D) Nile blue A staining of R. glutinis Phase contrast and fluorescence micrographs of R. glutinis cells grown at the indicated growth time intervals. (E) TAG synthesis in R. glutinis. Metabolic labeling of yeast cells with [$^{14}$C]acetate and its incorporation into TAG, DAG, free fatty acids, and PL at various time intervals was performed. Incorporation and analysis of labeled lipids was carried.

The invention is described in details hereafter and the examples provides are for illustration purposes only without any intention to limit the scope of the invention.

Materials and Methods

Materials—*Rhodotorula glutinis* (MTCC 1[2-$^3$H]G3P (12 Ci/mmol), [1-$^{14}$C]fatty acid (55 mCi/mmol) and [$^{35}$S]protein labeling mix were obtained from New England 151) was obtained from Institute of Microbial Technology, Chandigarh, India. [1-$^{14}$C]Palmitoyl-CoA (51 mCi/mmol), [1-oleoyl-9,10-$^3$H]LPA ((50 Ci/mmol), [glycerol-U-$^{14}$C]PA (100 mCi/mmol), Nuclear. [1-$^{14}$C]sodium acetate (56.4 mCi/mmol) was from Board of Radiation and Isotope Technology, Mumbai, India. Superose 12 (10/30) FPLC column and gel filtration molecular mass standards were from Pharmacia Biotech. Protein assay reagents were obtained from Pierce. Thin layer chromatography plates were from Merck. All other reagents were obtained from Sigma.

Growth conditions—*R. glutinis* cells were grown to the logarithmic phase in malt-yeast extract medium (pH 7.0) containing 0.3% yeast extract, 0.5% peptone, 0.3% malt extract supplemented with 1% glucose for 21 h with aeration at 30° C. Cell density was determined by colony-forming unit of each culture (one $OD_{600\ nm}$=3×10$^7$ cells).

*Saccharomyces cerevisiae* cells were grown in yeast extract-peptone and dextrose medium (pH 7.0) containing 0.3% yeast extract, 0.5% peptone supplemented with 1% dextrose with aeration at 30° C.

Human hepatocellular carcinoma cells (HepG2) were obtained from American Type Culture Collection (ATCC) and maintained in DMEM, supplemented with 39 mM sodium bicarbonate, penicillin (100 U/ml), streptomycin (100 U/ml), gentamycin (50 U/ml), cystatin (5 U/ml) and 10% (v/v) FBS. The cultures were grown at 37° C. in a humidified incubator containing 5% $CO_2$. HepG2 cells were stored frozen (in liquid nitrogen) to be able to revive them when required. The cells in logarithmic phase of growth were centrifuged at 300×g and the cell pellet was resuspended in ice cold freezing mixture (50% DMEM, 40% FBS and 10% DMSO) by dropwise addition and transferred to −70° C. and subsequently to liquid nitrogen. For reviving the cells, the vials were removed from liquid nitrogen and warmed rapidly to 37° C. Freezing mixture was removed by centrifugation at 300×g and the cells transferred to culture flasks containing 5 ml DMEM.

Animals: Brown adipose tissue, White adipose tissue and liver tissue—Six male Wistar rats, reared at 25–28° C., weighing about 200 g were obtained from Central Animal Facility, Indian Institute of Science, Bangalore. On the day of arrival (day 0), the rats were divided into two groups. One group (3 rats) was placed in separate cages and transferred to a cold room (4–6° C.; 12 h light/12 h dark) for 5 weeks, ad libitum. The rats in the other group were kept under normal animal house conditions at an ambient temperature of 25–28° C. After 5 weeks of cold treatment, the rats were decapitated, the intrascapular and cervical brown fat, liver and white fat surrounding the digestive tract was quickly dissected out and placed in preweighed vials, wet weight determined and frozen in liquid nitrogen. The tissues were stored at −80° C. At appropriate time, 1 g of the tissues were thawed, suspended in lysis buffer containing 1 mM EDTA and homogenized with four to five strokes in a Potter-Elvehjem glass-Teflon homogenizer followed by sonication (5 min at 50% duty cycle, power setting of 8, Vibra cell, Sonics materials). The homogenates were precleared by centrifugation at 300×g for 15 min. The supernatant was subjected to centrifugation at 10,000×g for 15 min. The supernatant (10,000×g) thus obtained was centrifuged at 240,000×g for 60 min to obtain the soluble fraction (cytosol). The pellet was washed with the lysis buffer and centrifuged again at 240,000×g for 60 min to obtain membranes. All the operations were carried out at 4° C.

Incorporation of [1-$^{14}$C]acetate into TAG—*R. glutinis* cells (8×10$^7$ cells/ml of 10 mM Tris-HCl, pH 8.0) were labeled with 2.5 μCi of [1-$^{14}$C]acetate for 2 h. Cells were harvested by centrifugation and the cell pellet washed with ice-cold lysis buffer. To the pellet, 0.5 ml of 10% acetic acid in isopropanol was added and boiled for 5 min. To the mixture, 1 ml of hexane was added and vortexed thoroughly. The hexane layer was removed, concentrated and the lipids were separated on silica gel G thin-layer plates developed with neutral lipid solvent system—petroleum ether: diethyl ether: acetic acid (70:30:1, v/v). Lipids were identified by their migration with standards (TAG, FFA, DAG, PC) and then scraped from the plate and counted in liquid scintillation counter.

Preparation of subcellular fractions—Logarithmic phase cells (*R. glutinis*—21 h and *S. cerevisiae*—15 h grown) (10 g wet weight) were suspended in minimum volume of 10 mM Tris-HCl (pH 7.5), 0.1 M NaCl, 5 mM $MgCl_2$, 1 mM phenylmethylsulfonyl fluoride, 100 μM leupeptin and 5% sucrose (~1 g wet weight cells/ml buffer). The cells were lysed using glass beads (0.45–0.6 μm) in the absence of detergent. Differential centrifugation was used to fractionate intracellular components. The supernatant (10,000×g) thus obtained was centrifuged at 240,000×g for 60 min to obtain the soluble fraction (cytosol). The pellet was washed and resuspended in lysis buffer and centrifuged again at 240,000×g for 60 min to obtain the pellet (membranes). All the operations were carried out at 4° C.

Enzyme assays—The assay mixtures consisted of all the components of lysis buffer except protease inhibitors; with labeled acyl donor, 20 μM [1-$^{14}$C]palmitoyl-CoA (100,000 dpm), 5 to 25 μg enzyme and 0.1 mM G3P for G3P acyltransferase or 50 μM LPA (1-oleoyl) for LPA acyltransferases or 50 μM 1,2-diolefin for DAG acyltransferase in a total volume of 100 μl. The incubation was carried out at 30° C. for 30 min and stopped by extracting lipids as described above. Lipids were separated on silica-TLC plates using petroleum ether:diethyl ether:acetic acid (70:30:1, v/v) and phospholipid solvent system—chloroform:methanol:acetic acid:water (170:25:25:4, v/v) as the solvent systems for separating neutral lipids and phospholipids, respectively. The lipids were visualized with iodine vapor and spots corresponding to LPA, PA, DAG and TAG scraped off for measurement of radioactivity in liquid scintillation counter (Wallac 1409 liquid scintillation counter) using toluene based scintillation cocktail containing 0.5% POP and 0.05% POPOP. In addition, acyltransferases were also assayed using labeled acyl acceptors [2-³H]G3P (50 µM, 100,000 dpm) for G3P acyltransferase or [1-oleoyl-9,10-³H]LPA (50 µM; 150,000 dpm) for LPA acyltransferase along with 20 µM palmitoyl-CoA. PA phosphatase activity was measured by monitoring the formation of DAG from [glycerol-¹⁴C(U)]PA (dipalmitoyl) (1.1×10⁵ dpm).

ACP and acyl-ACP synthetase assays were carried out as described (22). The reaction mixture consisted of 0.1 M Tris-HCl (pH 8.0), 0.4 M LiCl, 5 mM MgCl$_2$, 5 mM ATP, 1 mM DTT, 0.2% Triton X-100, [1-¹⁴C]palmitate (0.5 µCi) and 25–50 µg enzyme source in a final volume of 100 µl. The reaction mixture was incubated at 30° C. for 30 min. The amount of labeled acyl-ACP formed was determined by spotting the reaction mixture on Whatman no. 3MM and washed the filter paper thrice (10 min each wash) with chloroform:methanol:acetic acid (3:6:1, v/v) followed by liquid scintillation counting using toluene based scintillation cocktail containing 0.5% PPO and 0.05% POPOP.

The in gel superoxide dismutase assay was performed as described below. The purified TBC from *R. glutinis* or *E. coli* lysates, transformed as well as untransformed, were run on a 7% native PAGE at 4° C. The gel was soaked in a solution containing 0.025% nitro blue tetrazolium (NBT) and 0.01% riboflavin for 20 min in dark. The gel was then soaked in a solution containing 0.01% (w/v) TEMED for 5 min and exposed to intense light. The band position of SOD was white in the dark blue background of the gel.

Sucrose density gradient—The soluble fraction of (75–100 mg/0.5 ml) or the purified complex (~50 µg) of *R. glutinis* was layered onto a 10 to 30% linear sucrose gradient containing 10 mM Tris-HCl (pH 7.5), 5 mM MgCl$_2$ and 0.1 M NaCl. The tubes were centrifuged for 18 h at 200,000×g (Beckman SW 41 rotor). After the centrifugation, fractions (1 ml) were collected and assayed for TAG biosynthetic enzyme activities as described previously.

Purification of TAG biosynthetic enzyme complex—All operations were conducted at 4° C. except FPLC purification step, which was conducted at ambient temperature. The soluble fraction from the exponentially growing *R. glutinis* cells was used for the purification. Cytosol was loaded onto a 7% native polyacrylamide gel and electrophoresed under constant current at 4° C. After the run, the resolving gel was progressively cut into 0.5 cm slices and the protein was eluted by finely crushing the gel pieces in 10 mM Tris-HCl (pH 7.5) buffer containing 0.1 M NaCl, 5 mM MgCl$_2$ and 5% sucrose, and incubating overnight at 4° C. The gel eluted protein was used for further studies.

Size exclusion chromatography—The soluble fraction from *R. glutinis* was concentrated (2 mg protein/ml) and applied onto a preparative Superose 12 FPLC column fitted with Bio-Rad BioLogic low-pressure chromatography system. The column was pre-equilibrated with 10 mM Tris-HCl, pH 7.5 containing 0.1 M NaCl and the elution was with the same buffer at a flow rate of 0.3 ml/min. Fractions (1 ml) were collected and assayed for TAG biosynthetic enzyme activities (LPA acyltransferase, PA phosphatase and DAG acyltransferase). The column was calibrated with standard $M_r$ markers—apoferritin (440,000 Da), amylase (200,000 Da), yeast alcohol dehydrogenase (150,000 Da), bovine serum albumin (66,000 Da) and carbonic anhydrase (29,000 Da).

Antisera production—Rabbits were immunized by subcutaneous injection of 250 µg of *R. glutinis* purified ACP emulsified in Freund's complete adjuvant (FCA). Two booster doses of 125 µg protein emulsified in Freund's incomplete adjuvant (FIA) were administered at 3 weekly intervals. Ten days after the last injection, blood was collected, serum separated and stored at −20° C.

The major peptide, CY-ALELQADDFNK peptide SEQ ID NO: 2 corresponding to LPA acyltransferase and phosphatidic acid phosphatase peptides (major peptide CY-NAL-TGLHMGGGK peptide SEQ ID NO: 4, and minor peptide C-YVEGARP peptide SEQ ID NO: 6) and peptide SEQ ID NO: 7 of diacylglycerol acyltransferase from *R. glutinis* were conjugated to bovine serum albumin using m-maleimidobenzoyl-N-hydroxysuccinimide ester (18). The conjugated peptides (300 µg) were emulsified and injected into rabbits. The antibody production, specificity and titer were analyzed by ELISA (19). Proteins were separated by gel electrophoresis and transferred onto a nitrocellulose membrane for immunoblotting as described (20).

Cross-linking of proteins—Cross-linking was carried out as described (reference). Preparations of the *R. glutinis* purified complex (5 µg) were mixed with disuccinimidyl suberate to a final concentration of 0.5 mM in a total volume of 50 µl. The cross-linking was performed for 60 min at 4° C. The reaction was stopped by the addition of 5 µl of 0.25 M Tris-HCl, pH 7.5. The cross-linked products were resolved on 6% SDS-PAGE and electroblotted onto a nitrocellulose membrane. The membrane was probed with anti-ACP and anti-LPA acyltransferase antibodies for the detection of cross-linked products.

Protein labeling and immunoprecipitation—Logarithmic phase *R. glutinis* or *S. cerevisiae* cells (10⁷ cells/ml) were labeled with 30 µCi/ml of [³⁵S]protein labeling mix for 3 h at 32° C. The labeled cells were lysed and centrifuged at 10,000×g for 15 min to obtain the lysate. Primary antibodies were incubated with lysate for 1 h and the immunocomplex was precipitated with Protein A beads. The bound proteins were analyzed by gel electrophoresis followed by autoradiography.

Nile blue A staining—A smear of cells was prepared on a glass slide and heat fixed. The slides were immersed in 1% aqueous solution of Nile blue A stain for 10 min at 30° C. The slides were washed with water and air-dried followed by visualizing under fluorescence microscope.

Indirect immunofluorescence—Logarithmic phase (21 h) *R. glutinis* cells were fixed with 4% para-formaldehyde for 20 min followed by 4% formaldehyde for 60 min. The fixed cells were washed thrice with 0.1 M phosphate buffer (pH 5.9) and resuspended in 50 mg lytic enzyme with 1.2 M sorbitol for 6 h at 30° C. to obtain spheroplasts. The cells were washed, resuspended (10⁷ cells/ml) and plated on 12 mm coverslips, which were pretreated with poly-L-lysine. The coverslips coated with *R. glutinis* spheroplasts were treated with ice-cold methanol and acetone. The primary antibodies were added with a dilution of 1:10 except for anti-ACP antibody, which was used at a dilution of 1:200. Secondary antibody FITC/TRITC conjugates were used for detection. The slides were viewed in a confocal laser-scanning microscope (Leica TCS SP, Heidelberg, Germany) to locate TBC.

EXAMPLE I

Figure 1B:
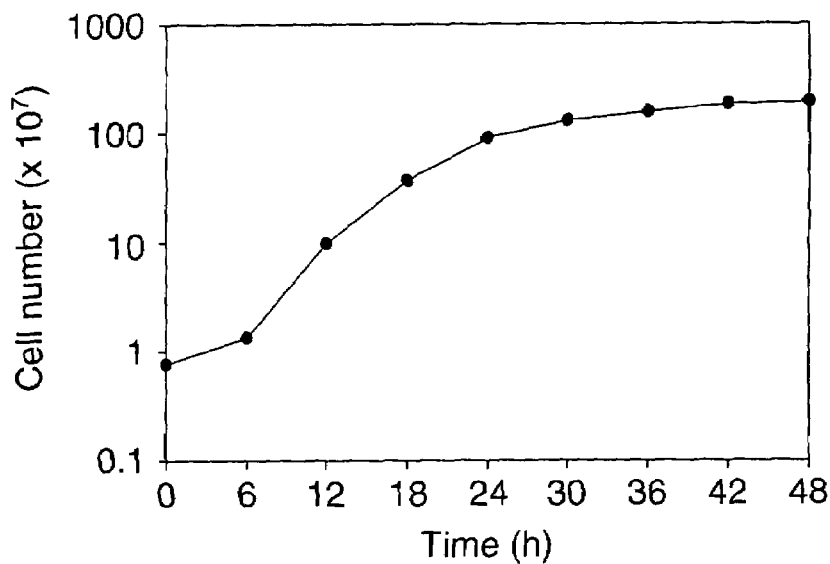
Figure 1C:
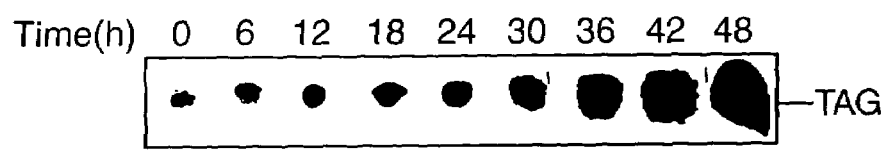
Figure 1D:
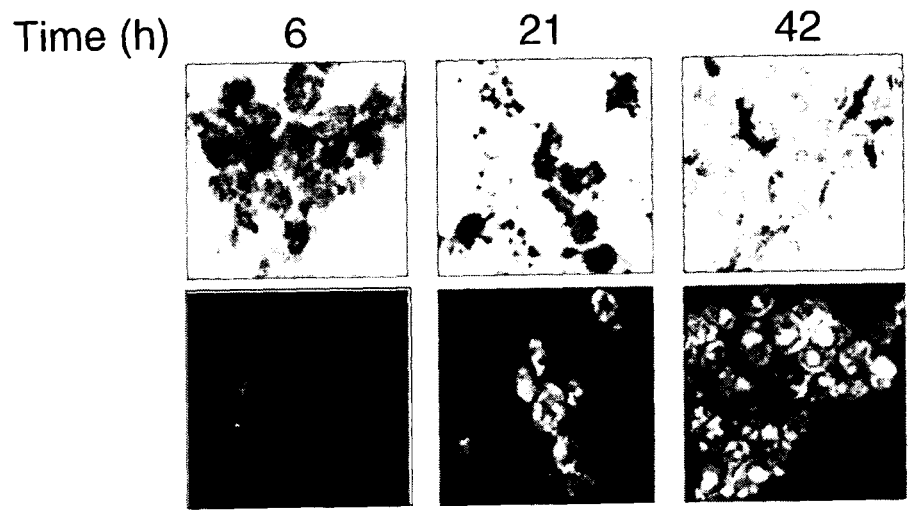
Figure 1E:
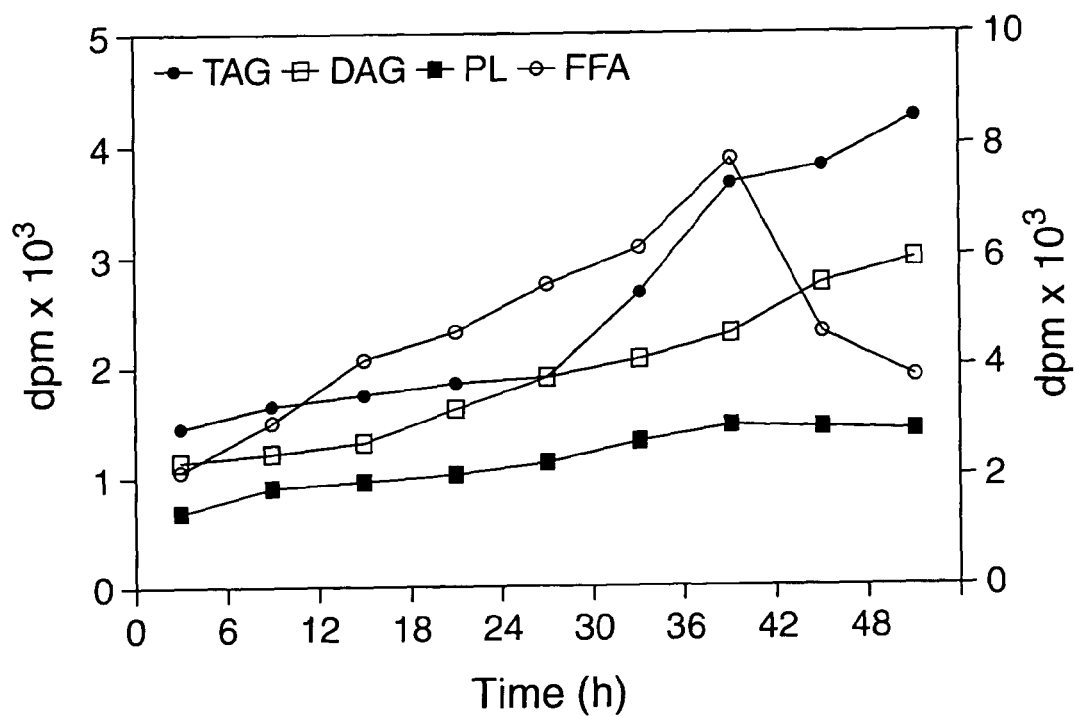

Growth, TAG synthesis in oleaginous yeast—The growth of oleaginous yeast cells were monitored by both $OD_{600\,nm}$ and colony-forming units at 30° C., both $OD_{600\,nm}$ and viable cell count increased proportionally with time (FIG. 1A). Yeast cells grown at various time intervals were stained with fluorescent dye (Nile blue A) followed by phase contrast fluorescence microscopy of cells revealed that 24 h grown cells accumulate TAG to the lesser extent. However, stationary phase cells showed an intense Nile blue A staining (FIG. 1B) suggesting the large accumulation of TAG at the stationary phase. Cells were isolated from different growth time intervals and cell number was adjusted to give 2.0 $OD_{600\ nm}$. Lipids were extracted and separated by silica-TLC using neutral lipid solvent system and the results indicated that TAG accumulation was found even at the early logarithmic phase (FIG. 1C). To metabolically label TAG formation, [$^{14}$C]acetate incorporation was carried out at various growth time intervals using $8 \times 10^7$ cells/time point revealed that the active lipid synthesis occur at 21 h (FIG. 1D). These results indicated that exponentially growing (21 h) cultures are active in synthesizing TAG. Therefore, all subsequent experiments were carried out on 21 h cultures. Table 1 summarizes the enrichment of TAG biosynthetic enzyme activities in the soluble (cytosol) fraction. Of the various TAG biosynthetic enzymes assayed, the soluble fraction exhibited high amounts (49 to 69% total activity) of LPA and DAG acyltransferases, and PA phosphatase activities as compared to the corresponding enzymes in the particulate fraction (Table I). On the contrary, a negligible amount of glycerol-3-phosphate acyltransferase activity could be detected in the soluble fraction. The pattern of distribution of activities remained the same under different lysis procedures such as French press and sonication. These results indicated that an additional TAG biosynthetic pathway could exist in the soluble fraction. LPA and DAG acyltransferases and PA phosphatase activities are collectively represented as 'triacylglycerol synthase' (TAG synthase).

EXAMPLE II

Figure 2A:
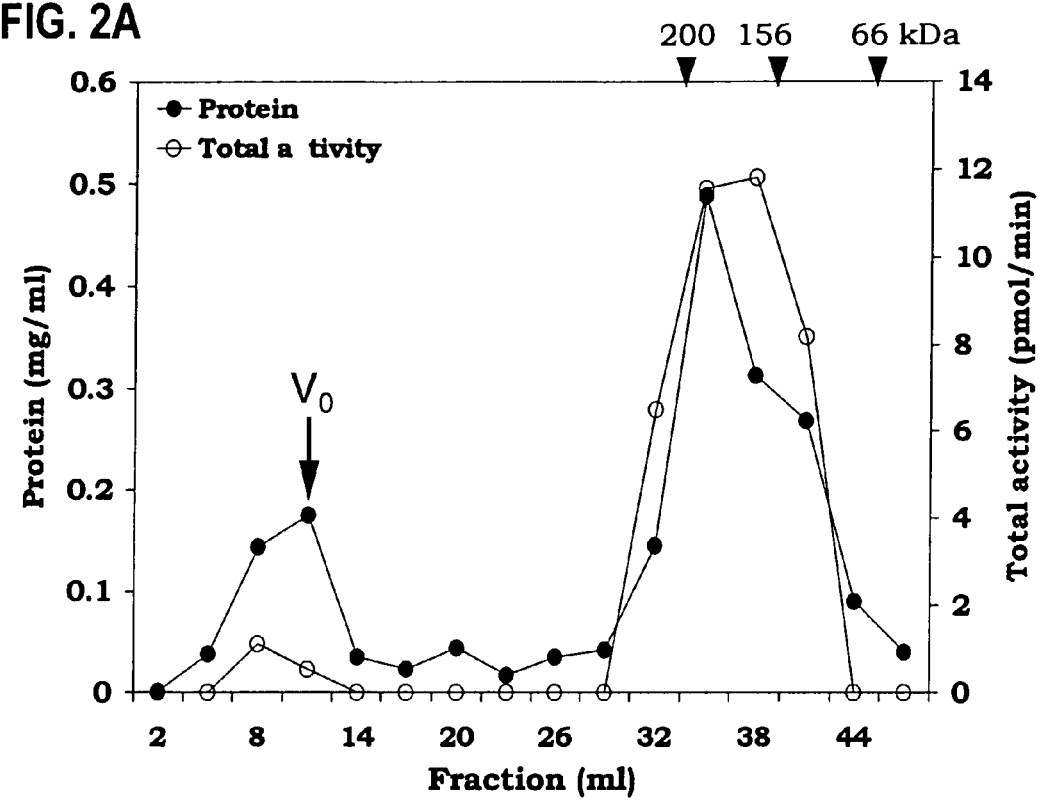
FIG. 2. (A) Identification of a soluble triacylglycerol biosynthetic enzyme complex. Cytosol was applied onto a Superose 12 gel filtration column and the elution profile of the TAG synthase activity (o) determined. (B) Cytosol was subjected to a 10–30% linear sucrose density gradient centrifugation. TAG synthase activity (LPAAT, PA phosphatase and DAGAT) (o) was estimated in 1 ml fractions and found to be co-localized in both the gel filtration and density gradient studies. Protein concentration (•) was estimated by Bradford's method for gel filtration and density gradient studies.

Identification of soluble TAG biosynthetic activity—The TAG synthase activity in the cytosol could be due to the presence of non-sedimentable cellular membrane fragments and lipid particles generated during isolation procedures. To demonstrate that the soluble fraction had TAG biosynthetic activity, which was loaded onto a gel exclusion column (Superose 12). TAG synthase activity (12–15%) was also found in the wide-volume fraction and this activity could be due the to the lipid particles. Most of the TAG synthase activity was eluted between 158 to 200 kDa gel filtration molecular weight standards (FIG. 2A). This experiment demonstrated that the TAG biosynthetic activity is soluble.

EXAMPLE III

Purification of TAG synthase—TAG biosynthetic activity was found high in the soluble fraction and this fraction was loaded onto a 7% native-polyacrylamide gel electrophoresis (PAGE) and the run was carried out at 4° C. To determine which region of the gel corresponds to TAG synthase, the eluted proteins were assayed for activity. LPA acyltransferase, PA phosphatase and DAG acyltransferase were detected in the same region of the gel (FIGS. 3A–B). To identify the number of bands present in the active gel eluted fraction, the same was reloaded onto a native gel and a single band was visualized upon silver staining. Overall summary of the purification procedure is shown in Table II. Native-PAGE step was effective and resulted in 469, 426-, and 409-fold purification for LPA acyltransferase, PA phosphatase and DAG acyltransferase, respectively, with the recovery of 39 to 56%. The ratio of acyltransferases to PA phosphatase activity remained constant during purification. Upon loading this fraction onto a Superose 12 column, the TAG synthase activity eluted as a single peak with the native molecular size of 180 kDa. The active fraction from gel filtration column contained LPA acyltransferase, PA phosphatase and DAG acyltransferase activities. These results suggested the possibility of an enzyme complex for TAG biosynthesis in *R. glutinis*.

EXAMPLE IV

Figure 2B:
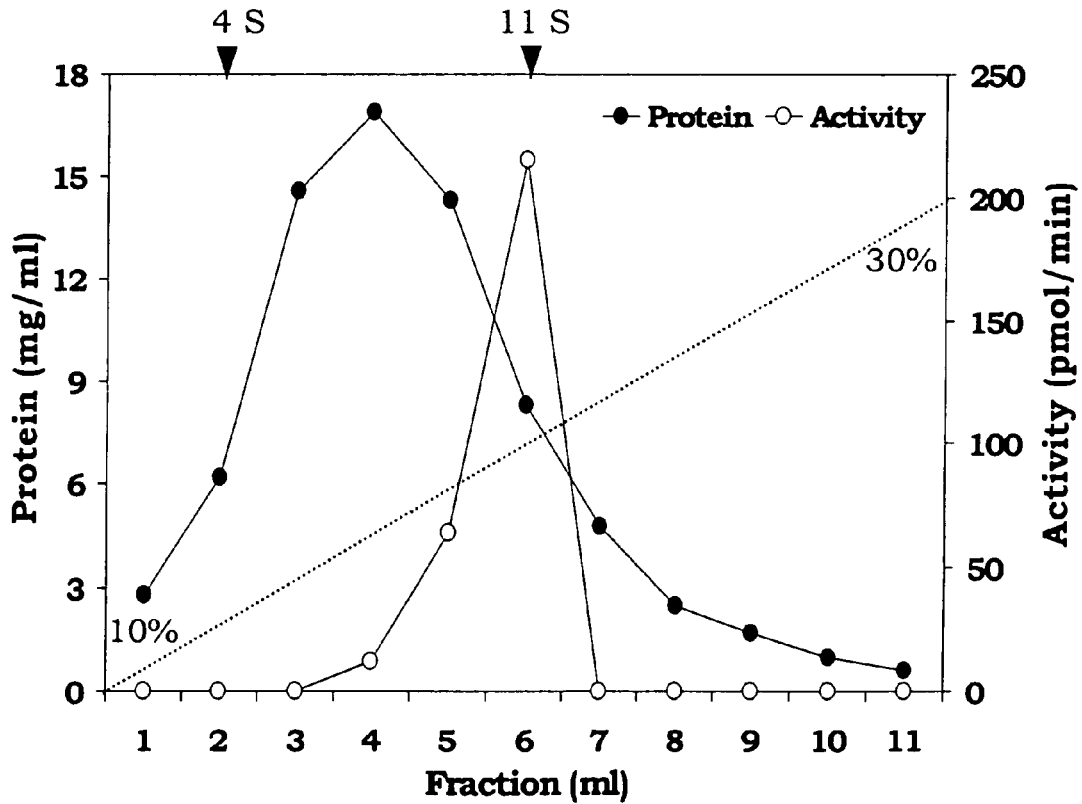

Identification of a 10S multienzyme complex—To examine if the enzymes were present as a multifunctional protein or multienzyme complex. Gel eluted active fraction containing TAG synthase were resolved under denaturing and reducing conditions on a polyacrylamide gel that showed five polypeptides upon silver staining (FIG. 3C). The purified complex was subjected to isoelectric focussing (IEF) followed by silver staining and the profile showed the presence of five polypeptides, of which four were basic (pI >8.0) and one was acidic (pI 4.0) proteins. The sedimentation value of the purified complex was estimated by loading the native polyacrylamide gel eluted active fraction onto a 10–30% linear sucrose gradient and the various fractions were analyzed for TAG synthase activity. The analysis revealed that LPA acyltransferase, PA phosphatase and DAG acyltransferase activities were associated with one fraction. The sedimentation value of the active fraction was calculated to be 10S (FIG. 2B). These data, in conjunction with the native-PAGE of the purified complex suggest the presence of a 10S-multienzyme complex for TAG biosynthesis in the cytosol of *R. glutinis*.

Figure 4A:
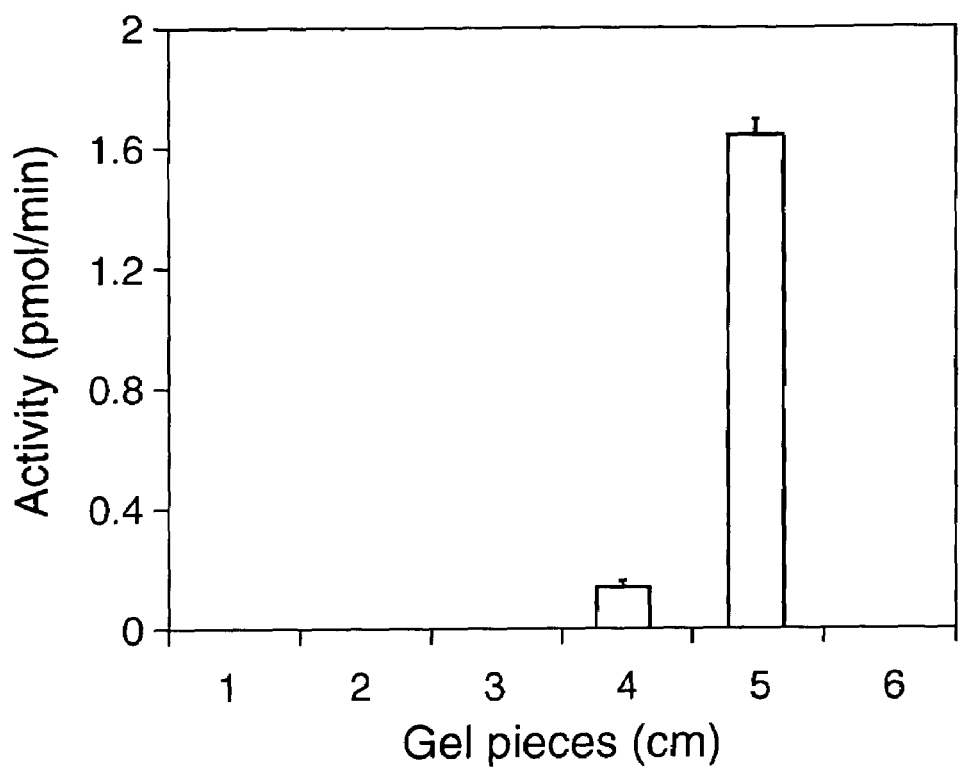
FIG. 4. (A) LPA acyltransferase and PA phosphatase are a part of the 10S TAG biosynthetic complex. Purified multienzyme complex was treated with 0.1% SDS and 50 mM DTT and electrophoresed on a 12% polyacrylamide gel. The resolving gel was progressively cut into 0.5 cm slices and the eluted protein (~20 µg) was assayed for TAG synthase activity. The $4^{th}$ and $5^{th}$ cm of the gel exhibited PA phosphatase and LPA acyltransferase activity, respectively. The apparent molecular mass of PA phosphatase corresponded to 48 kDa whereas LPA acyltransferase coincided with ~32 kDa. Values are the mean±SEM of four separate experiments, each performed in duplicate. (B) A synthetic peptide corresponding to the sequence of the major peptide of LPA acyltransferase (LPAAT) was conjugated to BSA for generation of polyclonal antibodies. The antiserum was used to probe the TBC, cytosol and CHAPS solubilized membranes after electrophoresis on native/SDS-polyacrylamide gels and subsequent transfer to nitrocellulose membrane. TBC and a 32 kDa protein were visualized in immunoblots under native and denaturing conditions, respectively. This antibody also reacted with a 28 kDa protein in the solubilized membrane fraction (lane 4). (C) [$^{35}$S]Labeled *R. glutinis* lysate was immunoprecipitated with anti-LPA acyltransferase antibody. The immunoprecipitate was analyzed on 7% native gel as well as 12% SDS-polyacrylamide gel and proteins visualized by fluorography. Native and SDS-gel fluorographs showed the presence of TBC and five polypeptides corresponding to the proteins of the TBC, respectively. Normal rabbit serum was used as the negative control in immunoprecipitations.

EXAMPLE V 10S complex and its polypeptide composition—To identify the nature of polypeptides in the complex, the purified 10S multienzyme complex was loaded onto a 12% SDS-PAGE in the presence of 0.1% SDS without boiling the sample and electrophoresed at 4° C. The gel was cut into 0.5-cm sections, protein eluted from the gel and assayed for TAG synthase activity. As shown in FIGS. 4A and D, LPA acyltransferase and PA phosphatase activities were predominantly found at the $4^{th}$ and $5^{th}$ cm, respectively and the yield was 7–10%. The gel-eluted LPA acyltransferase and PA phosphatase migrated separately with the molecular masses of 32 kDa and 48 kDa, respectively. DAG acyltransferase activity could not be localized in the gel. These results indicated that two of the polypeptides in the 10S TBC were LPA acyltransferase and PA phosphatase. The electrophoresed proteins were blotted onto PVDF membrane and the polypeptides corresponding to molecular sizes 32 and 48 kDa were excised, digested with trypsin and the tryptic peptide sequences determined. The internal sequences (Major peptide XALELQADDFNK, peptide SEQ ID NO: 1 and Minor peptide XXVNNVXPGXIEQ, peptide SEQ ID NO: 3) of LPA acyltransferase (32 kDa) did not match with any known sequences in the database. Tryptic peptide sequences (Major peptide NALTGLHMGGGK, peptide SEQ ID NO: 4 and Minor peptide YVEGARPXK, peptide SEQ ID NO: 5) of PA phosphatase (48 kDa) showed 40–100% identity with homosapien PA phosphatase 2a and 2b isoforms and with Musculus domesticus kidney PA phosphatase.

Figure 4B:
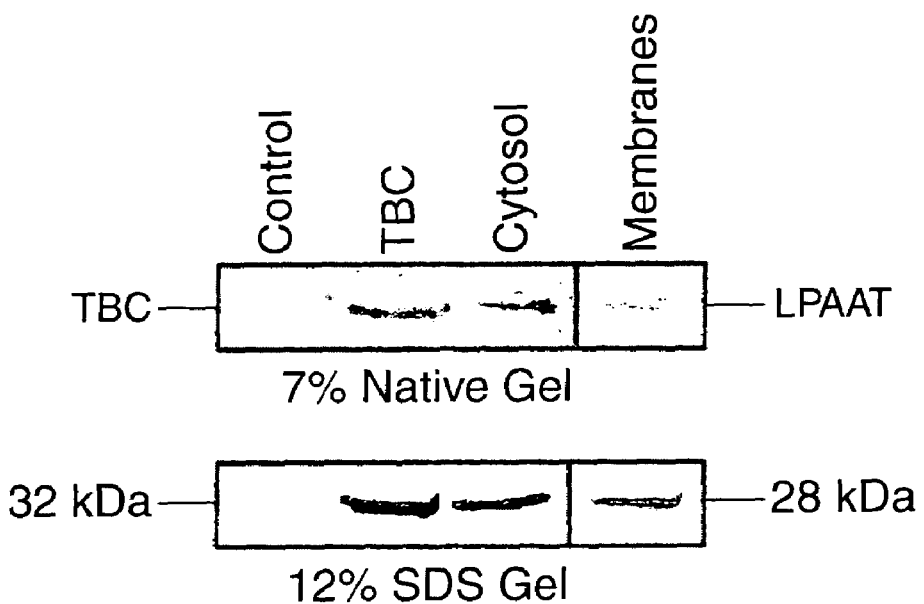

To confirm that 10S TBC contained LPA acyltransferase, immunoblots of native and SDS-polyacrylamide gels of proteins from purified complex, cytosol and membranes were probed with polyclonal antibodies raised against the major internal peptide of the cytosolic LPA acyltransferase. The antibody recognized the complex in the native immunoblot (FIG. 4B) and a single band of 32 kDa from the complex and the cytosol in the SDS polyacrylamide gel immunoblot (FIG. 4B). The same antibody was used for probing the 10 mM CHAPS solubilized *R. glutinis* microsomal membranes and was found to recognize a polypeptide in SDS gel of molecular size of 28 kDa. Similarly, immunoblots were carried out on purified complex, cytosol and solubilized membranes with polyclonal antibodies raised against two peptides of cytosolic PA phosphatase (FIG. 5). The antibodies for the major and minor peptides of PA Phosphatase recognized a single protein in the cytosol, which had a molecular mass of 48 kDa and 45 kDa protein in the microsomal membranes.

Figure 4C:
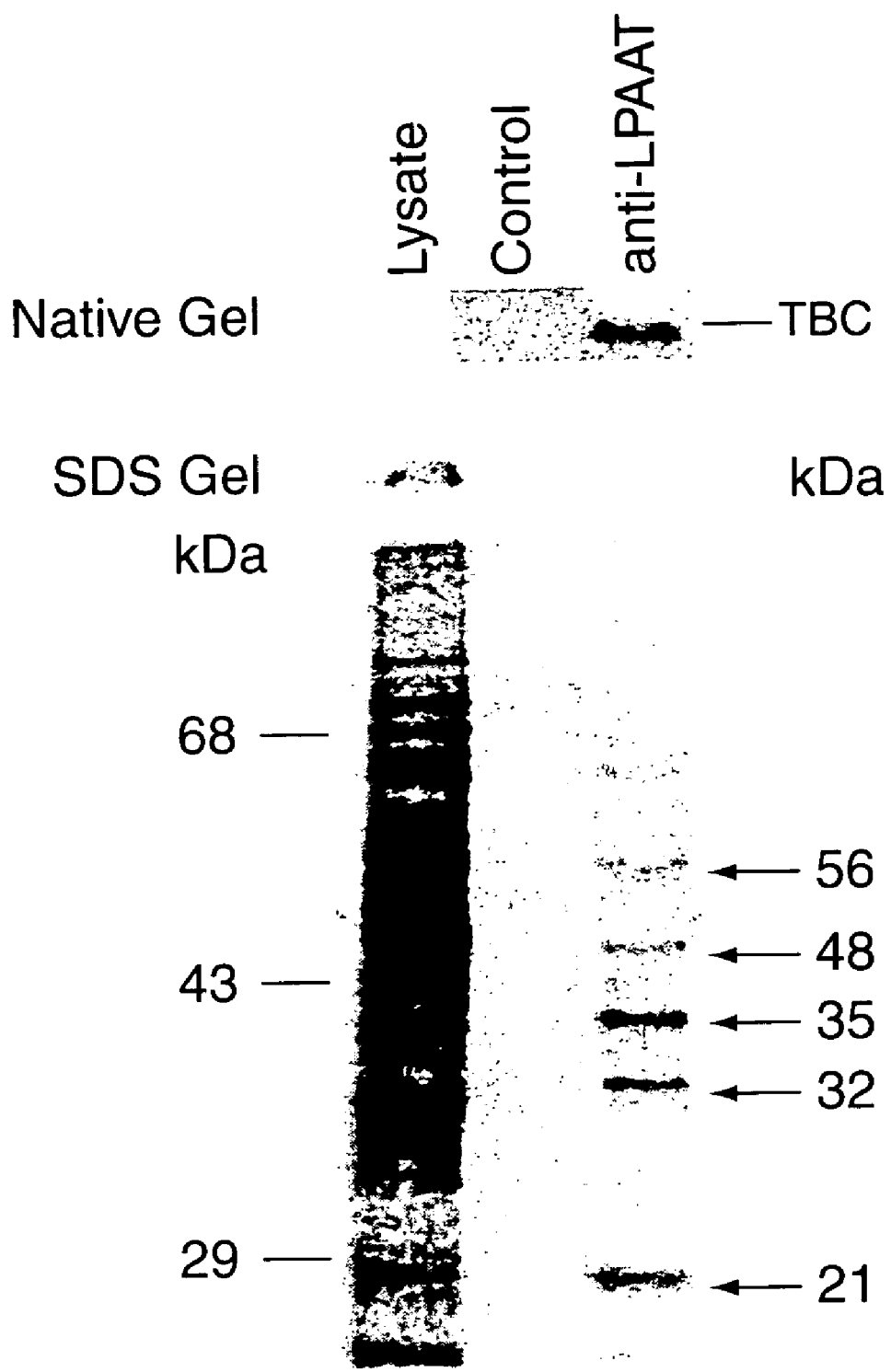
Figure 5A:
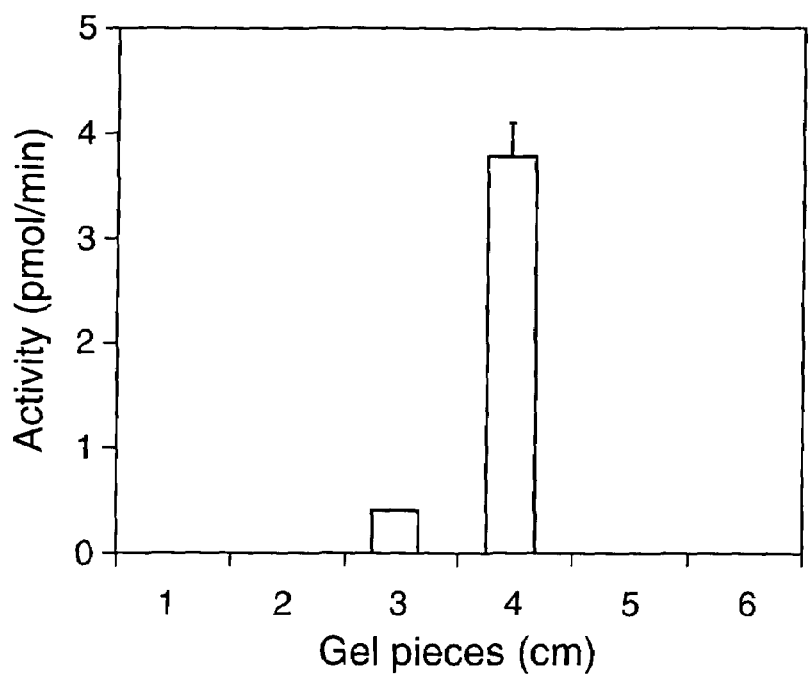
FIG. 5. (A) PA phosphatase is a part of the 10S TAG biosynthetic complex. Purified multienzyme complex was treated with 0.1% SDS and 50 mM DTT and electrophoresed on a 12% polyacrylamide gel. The resolving gel was progressively cut into 0.5-cm slices and the eluted protein (~20 µg) was assayed for TAG synthase. The $4^{th}$ cm of the gel exhibited PA phosphatase activity whose molecular size corresponded to 48 kDa. (B and C) Peptides were synthesized based on the internal sequences of PA phosphatase and polyclonal antibodies raised to these peptides. TBC, cytosol and 10 mM CHAPS solubilized membrane fraction was electrophoresed on native/SDS gels and transferred to nitrocellulose membranes, which were probed with PAPase antibodies. Both the antibodies recognized a 48 kDa protein under denaturing and TBC in nondenaturing conditions. PA phosphatase was found to be present in the membrane fraction as a 45 kDa protein (lane 4). (D) [$^{35}$S]Labeled *R. glutinis* lysate was immunoprecipitated with anti-LPAAT or anti-PA phosphatase (major and minor peptides) antibodies. The immunoprecipitates were analyzed on 7% native gel as well as 12% SDS-polyacrylamide gel and proteins visualized by fluorography. Native and SDS-gel fluorographs showed the presence of TBC and five polypeptides corresponding to the proteins of the TBC, respectively. Anti-PAPase 1 represents the antiserum to the PA phosphatase major peptide and anti-PAPase 2 to PA phosphatase minor peptide. Normal rabbit serum was used as the negative control (-ve) in immunoprecipitations.
Figure 5B:
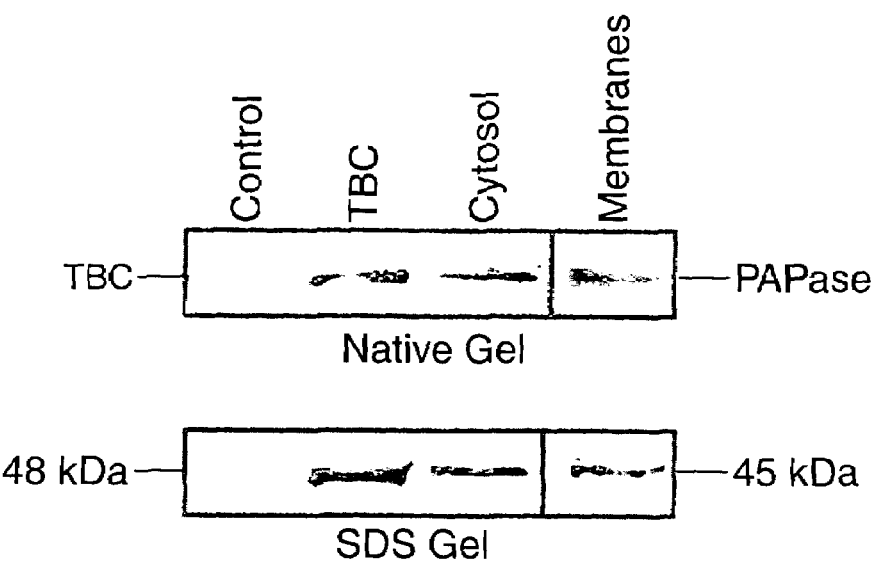
Figure 5C:
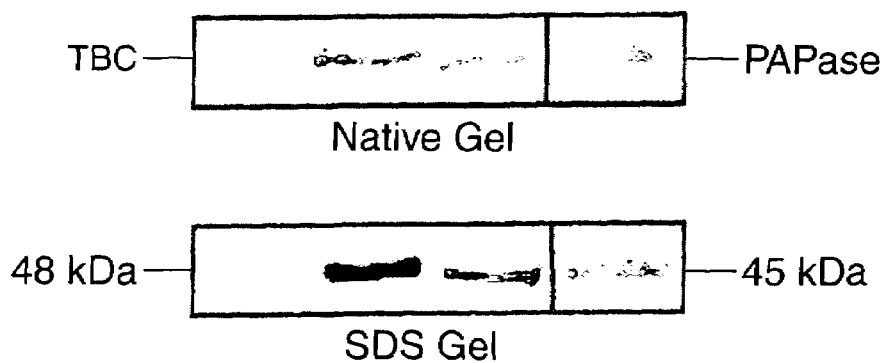
Figure 5D:
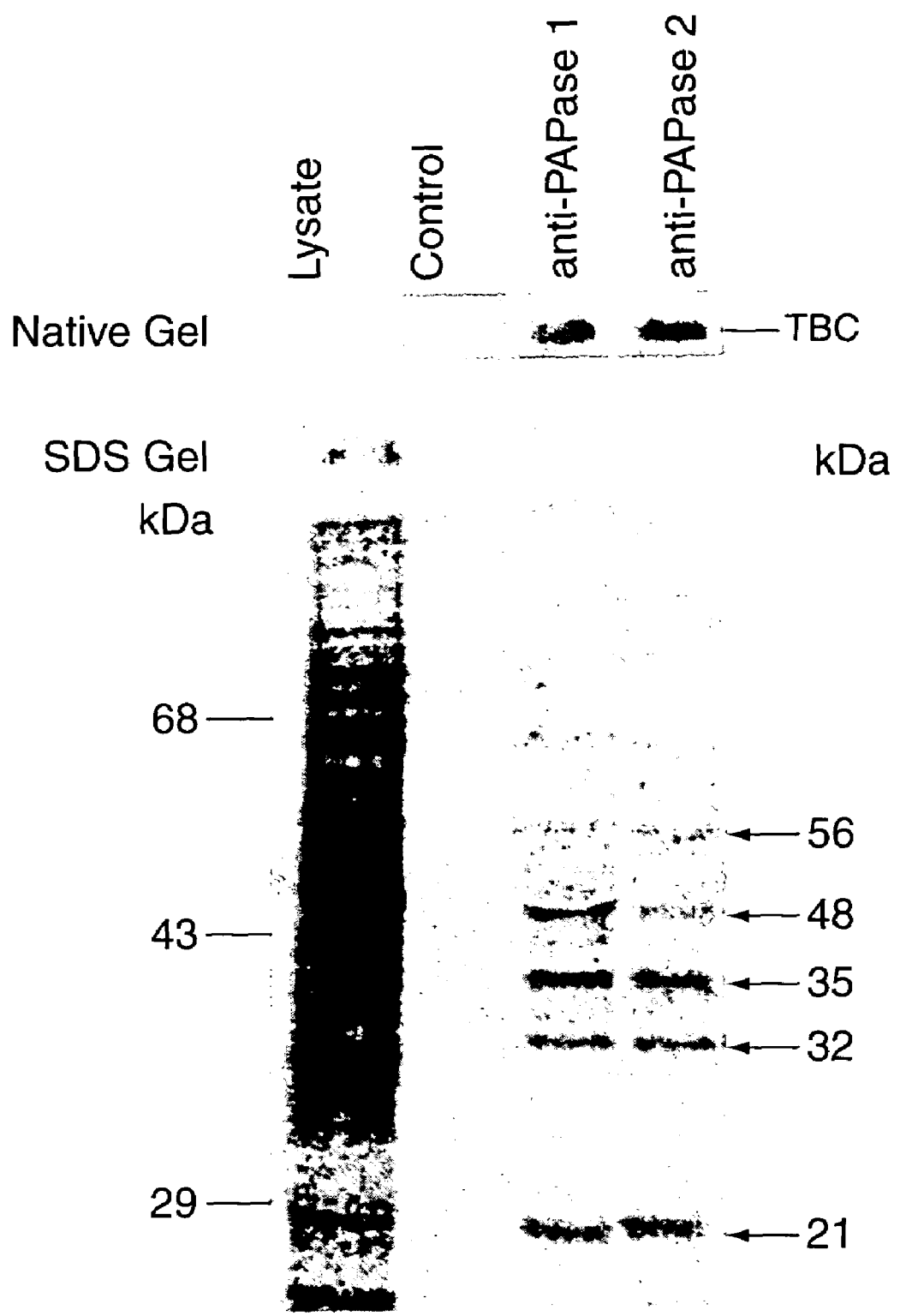

To determine whether the five different proteins identified in the TBC were held together by physical interactions, immunoprecipitations were carried out with antibodies raised to three peptides. All three peptide specific antisera, one to LPA acyltransferase and two to PA phosphatase specifically immunoprecipitated the TBC while normal rabbit serum or protein Sepharose A could not immunoprecipitate the complex. When the immunoprecipitate was resolved by SDS-PAGE followed by autoradiography, which exhibited five distinct bands corresponding to TBC (FIGS. 4C and 5D). Importantly, the autoradiograms of both native and SDS polyacrylamide gels were identical in all three cases. The presence of LPA acyltransferase, PA phosphatase and DAG acyltransferase was further confirmed by assaying for their activities in the immunoprecipitate (Table III).

DAG acyltransferase (56 kDa) polypeptide was microsequenced and the internal sequence (XLWAVVGAQPFG-GARGS, peptide SEQ ID NO: 7) showed 40–80% identity to the known DAG acyltransferase sequences available in the database. DAG acyltransferase was found to be the most labile enzyme of the 10S multienzyme TBC. The presence of DAG acyltransferase was confirmed by assaying the activity in the immunoprecipitate (Table III).

To study the formation of TAG, the purified complex was incubated with either [$^{14}$C]palmitic acid in the presence of ATP, MgCl$_2$ and LPA or [$^{14}$C]palmitoyl-CoA in the presence of LPA. Surprisingly, the rate of TAG synthesis was comparable with palmitic acid or palmitoyl-CoA indicating that the complex was capable of activating the fatty acid. The TBC preferred unsaturated long-chain fatty acids over saturated short chain fatty acids. The order of preference for free fatty acid as substrate by the TBC was linoleic>oleic>stearic>palmitic>myristic acids. During fatty acid synthesis, activation of fatty acids was shown to be via the formation of acyl-ACP in the cytosol (21). Fatty acyl-CoAs were the substrates for TAG biosynthesis and this activation was established in the microsomes. To examine the nature of fatty acid activation by the TBC, ACP was purified to homogeneity from *R. glutinis* as described (22) and polyclonal antibodies were raised to the purified ACP. To ensure that the 10S complex contained ACP, immunoblots of native and SDS-polyacrylamide gels of purified TBC were probed with antibodies to ACP purified from *R. glutinis*. The antibodies recognized a 21 kDa protein in Western blots and the complex under native conditions. The membrane fraction was devoid of ACP. The gene encoding for 21-kDa polypeptide was isolated and found that this polypeptide was superoxide dismutase.

EXAMPLE VI

Immunolocalization of TAG biosynthetic complex in the cytosol—To determine the subcellular localization of the TBC, *R. glutinis* spheroplasts were probed with anti-LPA acyltransferase, anti-PA phosphatase major and minor peptide, and anti-ACP antibodies for indirect immunofluorescence. The staining pattern revealed the cytosolic nature of TBC. PA phosphatase major peptide antibodies were found to have lower affinity than the antibodies to the minor peptide this was also evident upon immunostaining. The staining pattern for LPA acyltransferase and PA phosphatase was similar to ACP, which was used as the cytosolic marker. These results confirmed the cytosolic nature of the TBC. We have proposed a model for the TAG biosynthesis in *R. glutinis*.

EXAMPLE VII

Cytosolic TAG enzymes in other yeasts—In oleaginous yeast, the TAG biosynthetic enzymes were predominantly localized in the cytosol. In order to determine if the TAG biosynthetic enzymes are present in the soluble fraction in non-oleaginous yeast, subcellular distribution was performed on *S. cerevisiae* lysate. About 20% of the total TAG biosynthetic enzyme activities were found to be present in the soluble fraction (Table IV). LPAAT, PA phosphatase and DAGAT activities were detected in the cytosol. As compared to oleaginous yeast, the TAG biosynthetic enzymes in the non-oleaginous yeast are primarily localized in the membrane fraction however a small fraction of the enzyme activities is associated with the soluble fraction.

In an attempt to analyze the soluble TAG biosynthetic enzymes from *S. cerevisiae*, the cytosol and membrane fractions were resolved on SDS-polyacrylamide gels and the proteins transferred onto nitrocellulose membranes. The immunoblots were probed with the LPA acyltransferase, PA phosphatase and acyl-ACP synthetase antibodies (that were generated to *R. glutinis* proteins). Lysophosphatidic acid acyltransferase antibodies specifically recognized a 38 kDa polypeptide whereas acyl-ACP synthetase and PA phosphatase antibodies recognized a 30 and a 48 kDa polypeptide, respectively. The cytosolic isoforms were different from the membrane-bound TAG biosynthetic enzymes that have been reported previously. This also ruled out the possibility of any membrane contamination in the soluble fraction during cell lysis and differential centrifugation. To establish the nature of interactions between the TAG biosynthetic enzymes from *S. cerevisiae*, logarithmic phase grown cells were metabolically labeled with [$^{35}$S]methionine followed by obtaining the immunocomplexes with antibodies to LPA acyltransferase, PA phosphatase and acyl-ACP synthetase. All the three antibodies pulled down only their respective proteins. Protein A Sepharose or normal rabbit serum could not pull down any of these proteins. Resolution of the immunocomplexes by SDS-PAGE followed by fluorography revealed the presence of a 33, 48 and 30 kDa polypeptides being immunoprecipitated by the LPAAT, PA phosphatase and acyl-ACP synthetase antibodies. This exhibited that the soluble TAG biosynthetic enzymes of *S. cerevisiae* are not organized in the form of a complex. This was confirmed by assaying for the various enzyme TAG biosynthetic enzyme activities in the immunocomplexes. Hence, in non-oleaginous yeast, the soluble TAG biosynthetic enzymes exist as free enzymes.

EXAMPLE VIII

Cytosolic TAG Biosynthetic Enzymes in Mammalian Systems

TAG biosynthetic enzyme in HepG2 cells—TAG formation in the sub-confluent HepG2 cells showed that the particulate fraction contributed maximally to the biosynthesis of TAG. About 16–26% of the TAG synthesizing capacity was associated with the soluble (240,000×g supernatant) fraction. Table IV summarizes the TAG biosynthetic enzyme activity profile from the various fractions of HepG2 cells. Glycerol-3-phosphate acyltransferase activity could not be detected in either the soluble or the membrane fraction. The total activity of lysophosphatidic acid acyltransferase and phosphatidic acid phosphatase in the cytosolic fraction of HepG2 was slightly greater than diacylglycerol acyltransferase. The membrane fraction had considerable amount (74–84%) of TAG biosynthetic enzyme activity.

TAG biosynthetic enzyme activities in rat adipose tissue and liver—Adipose tissues are the classical oleaginous tissues. The profile of the TAG biosynthetic enzymes in the various fractions of the rat brown and white adipose tissues and the cold exposed rat liver were analyzed. Upon subcellular fractionation, cytosol, membrane and lipid body fractions were obtained. The cytosolic fraction of brown and white adipose tissues had ~20–35% of TAG biosynthetic enzyme activities as compared to the membrane fraction. As in HepG2 cells, total activities of LPA acyltransferase and PA phosphatase were higher in the soluble fraction as compared to DAG acyltransferase. A small amount of glycerol-3-phosphate acyltransferase activity could be detected in the membrane fraction of HepG2 cells. The cold treated rat liver TAG biosynthetic enzymes exhibited a modest increase in their activities over the untreated rat liver (25–26° C. maintained rats).

EXAMPLE IX

Generation and screening of TAG-deficient *R. glutinis* — Wild type cells were subjected to ethyl methane sulfonate mutagenesis to generate TAG biosynthesis mutants. Subjecting the mutagenized cells through a simple screen enhanced the TAG-deficient cell population. Due to accumulation of lipids, the wild-type (WT) cells float on 50% sucrose cushion whereas the mutagenized cells due to defective TAG biosynthesis have lost the property to accumulate TAG and thus pellet under the same conditions. The TAG-deficient cells thus obtained were stained with Nile blue A to determine the extent of lipid formation. In addition, the total lipid was extracted from all these mutants and the lipid profile was analyzed by silica-TLC using neutral and phospholipid solvent systems. Analysis of the neutral lipid profile of the mutagenized cells demonstrated that the mutants were defective in TAG production, as there was no visible TAG spot on the TLC. From the total pool of 610 mutants, about 20 mutants showed negligible neutral lipid formation. We chose two mutants TAG1 (high FFA, low DAG and TAG) and TAG2 (high FFA, DAG and low TAG) for further studies.

EXAMPLE X

Characterization of TAG biosynthetic mutants—TAG1 and TAG2 were characterized to determine the nature of defect in TAG biosynthesis. The growth rate of the WT oleaginous yeast cells and mutants at 30° C. was monitored by measuring the $OD_{600\ nm}$. The TAG1 and TAG2 mutants had almost similar growth pattern. The number of cells in the mutants were significantly low as compared to WT. Accumulation of TAG in 21 h grown cells indicated that the TAG amount was negligible in TAG1 and TAG2 as compared to the WT cells when observed by Nile blue A staining.

EXAMPLE XI

Labeling studies on TAG mutants—Logarithmic phase (21 h) yeast cells ($8\times10^7$ cells/ml) were labeled with 2.5 µCi [$^{14}$C]acetate or 2.5 µCi [$^{32}$P] orthophosphate 2 µCi [$^{14}$C] glycerol-3-phosphate or 2 µCi [$^{14}$C]oleic acid for 3 h at 30° C. Before labeling, [$^{14}$C]oleic acid was converted to its potassium salt by boiling the dried fatty acid in 10 µl of 4.5% KOH at 70° C. for 10 min. and then added to the cells. Prior to addition of [$^{14}$C]glycerol-3-phosphate, the cells were sonicated for 3 min at 50% duty cycle, power setting of 8, Vibra cell, Sonics materials. Cells were harvested by centrifugation and the cell pellet washed with ice-cold phosphate-buffered saline. To the pellet, 0.5 ml of 10% acetic acid in isopropanol was added and boiled for 5 min. To the mixture, 1 ml of hexane was added and vortexed thoroughly (19). The hexane layer was removed, concentrated and lipids were separated on silica gel G thin-layer plates developed with petroleum ether:diethyl ether:acetic acid (70:30:1, v/v) to separate the neutral lipids or chloroform:methanol:acetone:acetic acid:water (10:2:4:3:1, v/v) solvent system to resolve phospholipids. Lipids were identified by comparing their migration with the standards and the TLC plates were subjected to autoradiography. The individual spots were scraped off from the plate and the radioactivity measured in liquid scintillation counter.

Studies carried out on the incorporation of [$^{14}$C]acetate into lipids indicated that the incorporation of acetate into TAG and PC reached maximum at 3 h of labeling. At this time point, 22% of the radiolabel was associated with TAG, 18% with PC and 48% with FFA. Analysis of the neutral lipid profile of the cells indicated that both the mutants were defective in TAG production, as there was no visible TAG spot on the TLC autoradiograph. The pattern of incorporation of [$^{14}$C]acetate into lipids of WT, TAG1 and TAG2 was compared by silica-TLC. TAG1 accumulated only 6% and TAG2, 10% TAG as compared to the WT cells. In addition to negligible TAG, TAG1 also had significantly low DAG indicating a defective DAG synthesis. When the [$^{14}$C] acetate labeled lipids were resolved on TLC using phospholipid solvent system, TAG1 showed reduced PA as compared to the WT whereas the phospholipid profile of TAG2 was similar to that of the WT.

In an attempt to understand the biosynthesis of phospholipids, the mutants and the WT cells were labeled with [$^{32}$P]orthophosphate and the total lipids extracted and resolved on TLC using a phospholipid solvent system. TAG2 showed a higher amount of PC than the WT *R. glutinis*. On the other hand, TAG1 phospholipid profile indicated 60% decrease in the PA content of the cell, which corroborated with the [$^{14}$C]acetate labeling studies.

Incorporation of [$^{14}$C]oleate into TAG biosynthetic intermediates was determined for the WT and mutant yeast cells. The total lipids were resolved on TLC using neutral and phospholipid solvent systems. The neutral lipid profile of both the mutants indicated a significant decrease in the TAG content as compared to WT. TAG1 showed a 90% decrease whereas TAG2 an 86% decrease in the TAG content as compared to the WT. Incorporation of oleate into PL indicated that there was no obvious change in the PL pattern of TAG2 as compared to WT whereas TAG1 had compromised PA formation. Metabolic labeling of the WT and mutant yeast cells with [$^{14}$C]glycerol-3-phosphate yielded similar labeling pattern as obtained with [$^{14}$C] acetate.

EXAMPLE XII

Determination of the mutation in TAG1 and TAG2—In order to determine the defect in the TAG biosynthetic mutants, the individual TAG biosynthetic enzyme activities from the cytosol were measured as a function of time. TAG1 had a defective LPA acyltransferase and thus, there was a reduction in PA, DAG and TAG formation. The DAG acyltransferase and PA phosphatase activities were comparable to that of the WT enzyme activities. On the other hand, TAG2 had a defective DAG acyltransferase and thus, there was no TAG formation. These results indicated that the TAG1 had a defective LPA acyltransferase and TAG2 a defective DAG acyltransferase.

EXAMPLE XIII

Activities of the isoforms of TAG biosynthetic enzymes—To get an insight into the isoforms of enzymes of the TAG biosynthetic pathway, the cytosolic and the membrane-bound TAG biosynthetic enzymes were isolated from the mutants and WT and their activities measured. It was surprising to observe that the membrane-bound TAG biosynthetic enzyme activities were unaltered. WT and TAG mutants had comparable LPA and DAG acyltransferases, and PA phosphatase activities. The purified cytosolic LPA acyltransferase activity in TAG1 and DAG acyltransferase activity in TAG2 were significantly lower in the mutants than the corresponding WT enzyme activities. The loss of enzyme activities was comparable to the decrease in TAG accumulation in the mutants. This experiment led us to conclude that the cytosolic isoform of LPA and DAG acyltransferases were defective in the mutants, thereby resulting in reduced TAG formation.

EXAMPLE XIV

Cytosolic TAG biosynthetic enzyme profile of TAG1 and TAG2—The TBC from the TAG biosynthetic mutants was isolated and analyzed by SDS-PAGE. The gel profile of TAG1 was identical to that of the WT indicating that defective enzyme was present as a part of the TBC. However, TAG2 had a reduced DAG acyltransferase as compared to WT cells. To establish the apparent difference observed in the LPA and DAG acyltransferase on SDS-polyacrylamide gels, immunoblotting was performed on the purified TBC from the WT, TAG1 and TAG2 under native and denaturing conditions. There was no evident change in the LPA acyltransferase from the TBC and cytosol of TAG1 and TAG2 when compared to the WT. PA phosphatase enzyme profile monitored by the PA phosphatase major and minor peptide antibodies indicated that there was no change in the amount of this enzyme in the cytosol and the TBC of TAG1 and TAG2 when compared to the WT enzyme. DAG acyltransferase was comparable in WT and TAG1 cells whereas, there was a considerable decrease (39–48%) in the amount of cytosolic DAG acyltransferase in the TAG2 mutant.

EXAMPLE XV

Identification of acyl-ACP synthetase—To understand the mechanism by which fatty acids were utilized by the TBC to generate TAG, we examined the formation of acyl-ACP and acyl-CoA. The formation of acyl-ACP was monitored by performing the acyl-ACP synthetase assay with $[1-^{14}C]$ linoleic acid or $[1-^{14}C]$palmitic acid and resolving the reaction mixture on SDS-polyacrylamide gel followed by fluorography. It was evident that acyl-ACP was formed. Incubation of the purified TBC with $[1-^{14}C]$linoleic acid or $[1-^{14}C]$oleic acid or $[1-^{14}C]$stearic acid or $[1-^{14}C]$palmitic acid in the presence of 5 mM ATP further confirmed the formation of acyl-ACP by the TBC. Among the fatty acids tested, linoleic acid exhibited higher activity as compared to other fatty acids. These results demonstrated that the complex was capable of acylating ACP and this could be due to the presence of acyl-ACP synthetase. However, the formation of acyl-CoA was not detected under the standard assay conditions. In order to identify acyl-ACP synthetase in the complex, photoaffinity labeling with $[^{32}P]$azido-ATP was carried out and it was observed that the azido-ATP was covalently bound to a 35 kDa polypeptide under denaturing and reducing conditions (FIG. 1C). These results indicate the presence of acyl-ACP synthetase in the triacylglycerol biosynthetic complex of R. glutinis.

EXAMPLE XVI

Purification of acyl-ACP synthetase—Acyl-ACP synthetase activity was found only in the soluble fraction of R. glutinis and this fraction was electrophoresed on a 7% native-polyacrylamide gel. Acyl-ACP synthetase, LPA acyltransferase, PA phosphatase, DAG acyltransferase and ACP were detected in the same region of the gel. The native polyacrylamide gel electrophoresis step was very effective and resulted in a 358-fold purification of acyl-ACP synthetase, with a recovery of 42%. The specific activity was determined to be 494 pmol min$^{-1}$ mg$^{-1}$ for palmitic acid while the total activity was 5.43 pmol min$^{-1}$. The purity of the complex was determined by 2-dimensional electrophoresis. Acyl-ACP synthetase was further purified to homogeneity from the TBC by subjecting the native polyacrylamide gel eluted active fraction to SDS-PAGE. The 35-kDa band, which corresponded to acyl-ACP synthetase, was excised out of the SDS-polyacrylamide gel, protein eluted and reloaded onto a 12% SDS-polyacrylamide gel. A single band of $M_r$ 35-kDa was observed upon silver staining. Although the enzyme preparation was pure, the specific activity dropped to 60 pmol min$^{-1}$ mg$^{-1}$ and the yield was 1.1%. The pI of acyl-ACP synthetase was estimated to be ~8.7 by isoelectric focussing and 2D gel electrophoresis. The purified protein was subjected to N-terminal sequencing and the sequence VHLAVALYGLAAVRVSRIVR, (peptide SEQ ID NO: 8) showed 46% similarity towards the 276–295 amino acid region of the putative acyl-ACP synthetase from Campylobacter jejuni. The N-terminal sequence of R. glutinis acyl-ACP synthetase did not show any similarity to the E. coli 2-acyl-glycerophosphatidylethanolamine acyltransferase/acyl-ACP synthetase.

EXAMPLE XVII

Properties of acyl-ACP synthetase—Maximum enzyme activity was observed in the presence of both fatty acids and LPA in the reaction mixture. Labeling of acyl-ACP synthetase with $[\gamma-^{32}P]$ATP was maximum when both the substrates were supplied in the reaction mixture. Enzyme-AMP complex was not detected in the absence of fatty acid. This suggested that the acyl-ACP synthetase from R. glutinis required both FFA and LPA in the presence of ATP to be maximally active. The acylation of ACP followed by synthesis of TAG by the TBC in the presence of exogenous ACP from either E. coli or R. glutinis and acyl-ACP synthetase were determined. The results indicated that exogenous supply of either ACP or acyl-ACP synthetase to the TBC had no significant effect in the TAG formation.

To establish that the 10S TBC contained acyl-ACP synthetase, the purified complex, the cytosol and the membranes were probed with polyclonal antibodies raised against the purified acyl-ACP synthetase by immunoblotting. The antibody recognized a single band of 35-kDa protein in the SDS polyacrylamide gel immunoblot from the complex as well as the cytosol. The same antibody was used for probing the 10 mM CHAPS solubilized microsomal membranes and found that there was no immunoreactive protein in this fraction suggesting the absence of this enzyme in the membranes. The antibodies reacted with *E. coli* acyl-ACP synthetase but did not show any reactivity towards acyl-CoA synthetase. When the *R. glutinis* acyl-ACP synthetase was probed with anti-ACP antibodies and found that the antibodies did not recognize the 35-kDa protein.

To validate whether acyl-ACP synthetase was a part of the TBC, logarithmic phase grown *R. glutinis* cells were metabolically labeled with [$^{35}$S]methionine followed by immunoprecipitation with acyl-ACP synthetase antibodies. The antibodies specifically immunoprecipitated the TBC while neither normal rabbit serum nor protein Sepharose A did not immunoprecipitate the complex. Resolution of the immunoprecipitate by SDS-PAGE followed by fluorography, exhibited five distinct polypeptides corresponding to TBC that contained 35 kDa acyl-ACP synthetase. This result demonstrated that acyl-ACP synthetase is indeed a part of the triacylglycerol biosynthetic complex.

The acyl-ACP synthetase antibodies were capable of inhibiting only 40% of the enzyme activity. The inhibition of the acyl-ACP synthetase activity with the antibodies subsequently reduced the TAG formation by the TBC. There was almost complete inhibition of acyl-ACP and TAG formation when the complex was pre-incubated with anti-ACP antibodies. This corroborated that one of the components of the 10S complex is indeed acyl-ACP synthetase.

The TBC was subjected to cross-linking using a homobifunctional cross-linker, disuccimidyl suberate, in order to rule out the possibility of any lipid-protein interactions. As we were unsuccessful in detecting the complex with anti-acyl-ACP synthetase antibodies, we probed the cross-linked product with ACP antibodies. It was observed that the cross-linked product migrated at ~200 kDa indicating that the complex was held together by protein—protein interactions.

EXAMPLE XVIII

Molecular cloning and sequence analysis of the cDNA's encoding SOD—One liter yeast cell culture was grown for 21 h and total RNA was isolated by following GITC method. mRNA was purified from total RNA using oligo (dT) cellulose column. The cDNA library was constructed from the purified mRNA using the cDNA library construction kit by following the manufacturer's protocol. The vector used for constructing the library was pBK-CMV ZAP expression vector and the cDNA was directionally cloned in EcoRI and XhoI sites. The cloned vector was packaged in Gigapack packaging extract provided by the manufacturer and propagated in host XL-1 blue MRF' *E. coli* cells. The titer of the amplified library was $10^{11}$ pfu/ml. N-terminal sequence of the 21 kDa protein (superoxide dismutase) was obtained by micro-sequencing of the protein transferred onto PVDF membrane following Edman degradation. Protein sequencing was performed using an Applied Biosystems gas phase sequenator at the protein sequencing facility of Rockefeller University. The nucleotide probes generated from protein sequence (AYNKIPAVALPKLPFATNAL, peptide SEQ ID NO: 12) were radiolabeled at the 3' end using TdT and [$\alpha$-$^{32}$P]dATP. Filters carrying $1\times10^5$ clones from *R. glutinis* cDNA library were hybridized with the radiolabeled probe. The positive λZAPII phage plaques, identified by autoradiography were purified through another two rounds of screening using the same probe. After the tertiary screening, three positive clones were obtained and in vivo excision was performed using a helper phage (ExAssist™). The clones obtained were sequenced by the dideoxy chain termination method using a Dye terminator cycle sequencing kit (PerkinElmer Life Sciences) with a DNA sequencer (Applied Biosystems Model 377). All the cDNAs were sequenced in both directions using T7 and T3.

Cloning of SOD—To obtain the full-length cDNA clone that encodes *R. glutinis* 21 kDa (ACP antibody reactive protein), *R. glutinis* cDNA library was screened with the oligonucleotide degenerate primer, 5'-TACAACAAGATC-CCIGTICTCCCTAAGCTCCCITTCGCITACAAC-3' (SEQ ID NO: 13), designed based on the N-terminal amino acid sequence of the protein, AYNKIPAVALPKLPFATNAL (peptide SEQ ID NO: 12). The nucleotide probe was radiolabeled at the 3' end using TdT and [$\alpha$-$^{32}$P]dATP. A large number of positive clones were isolated in the screen, and the plasmids from three clones that contained the longest inserts (~0.7 kb) were subjected to nucleotide sequencing. The sequences obtained were identical except a few base pairs changes from the 3'-untranslated regions. The complete primary structure of a cDNA (732 base pairs) is shown in FIG. 6. Analysis of the nucleotide sequence revealed an open reading frame of 191 amino acids, with translation initiating at the ATG codon at nucleotides 25–27 and consensus Kozak translation initiation sequence (GCCATGG). The 3'-untranslated region contained a noncanonical polyadenylation signal (AATAC) near the poly(A) tail (FIG. 6) indicating that the isolated clone represents full length cDNA. The calculated molecular mass of the *R. glutinis* protein is 20.9 kDa, close to that of estimated by SDS-polyacrylamide electrophoresis. When the sequence of N-terminal amino acid was aligned with the deduced amino acid sequence, there was a complete match, confirming that the cloned cDNA codes for 21 kDa protein (FIG. 6). Hydropathy plot of the predicted protein suggested there was no transmembrane domain, which is in agreement with the observation that TBC is located at the cytosol. When the deduced amino acid sequence of 21 kDa was examined for a number of structural motifs, we identified a single potential Asn-linked glycosylation site at $^{80}$NHTL$^{83}$ and a casein kinase II phosphorylation site at $^{187}$SLSE$^{190}$. In addition, there were six protein kinase C dependent phosphorylation sites and seven N-myristoylation sites. BLAST search for the deduced amino acid sequence in all the available databases for the isolated cDNA clone revealed that the protein is homologous to mitochondrial manganese-SOD. The deduced amino acid sequence shared more than 30% identity with *Ganoderma microsporum* (38%), human (33%) maize (31%), *S. cerevisiae* (29%) and *E. coli* (24%). In addition, we used the ClustalW program to obtain an optimized multiple sequence alignment of known manganese-SOD (FIG. 7). All protein posses three conserved domains I, II and III, the isolated clone showed homology to the domains I and II but not to domain III. This sequence has been submitted to GenBank™ with the identification as $Mn^{2+}$ superoxide dismutase. Phylogenetic analysis of SOD revealed that the protein is more closely related to *Ganoderma microsporum*.

Expression of Recombinant SOD—The SOD gene was transformed to *E. coli* JM109 cells independently and induced with 0.5 mM IPTG for 4 h. The crude cell lysate was sonicated and run in a 12% SDS-PAGE. Untransformed cell lysate was used as a control. The full-length *R. glutinis* cDNA in pBK-CMV expression vector containing T7lac promoter, which was then used to transform *E. coli* cells (JM109). Transformed bacteria were induced by treatment with IPTG to produce the recombinant protein. Protein extracts were prepared from the induced bacteria and assayed for SOD activity and found that there was no increase in SOD activity in JM109 cells transformed with the recombinant plasmid as compared to untransformed cells. SDS-polyacrylamide gel electrophoresis demonstrated that bacteria transformed with the recombinant plasmid contained a polypeptide of the expected size, whereas crude extracts of bacteria lacking *R. glutinis* SOD-coding sequence did not show the 25-kDa protein. Western blot analysis of the transformed JM109 cells with anti-ACP antibodies showed an intense signal at around 25 kDa and no signal was detected in the untransformed cells.

EXAMPLE XIX

Cloning of Acyl Carrier Protein—For ACP, screening was performed using polyclonal antisera raised against the purified *R. glutinis* ACP. To screen the expression library with antibody, plaques were grown for 4 h at 42° C. after plating and overlaid with IPTG soaked nitrocellulose membrane and incubated at 37° C. for 6–8 h. Membranes were developed by following the western blot procedure with primary antibody dilution 1:1000 in 0.5% gelatin in phosphate buffered saline containing 0.05% Tween 20. Three rounds of screening were performed and a cross-reactive 21 kDa SOD clones were eliminated by checking the tertiary positive clones with anti-SOD antibody. Three positive clones were sequenced as described above.

Cloning of Acyl Carrier Protein—To obtain the full-length cDNA clone that encodes *R. glutinis* ACP, *R. glutinis* cDNA expression library was screened with the antibodies raised against the purified ACP. A large number of positive clones were isolated in the screen, and the plasmids from three clones that contained the longest inserts (~0.7 kb) were subjected to nucleotide sequencing. The sequences obtained were identical except a few base pairs changes from the 3'-untranslated regions. The complete primary structure of a cDNA is shown in FIG. 8. BLAST search for the deduced amino acid sequence in all the available databases for the isolated cDNA clone revealed that the protein is homologous to ribosomal protein (FIG. 9).

Expression of ACP in *E. coli*—To prepare a vector suitable for expression of recombinant ACP in *E. coli*, we first generated an 351-bp DNA fragment containing the coding sequence for ACP by PCR of the aforementioned cDNA clone using forward primer (5'-CGAAGCTAGCAT-GAAGCACGTCGCCGCCTACCTC-3', SEQ ID NO: 14) and reverse primer (5'-GCGAATTCTTAGTCGAA-GAGACCGAAGCCCAT-3', SEQ ID NO: 15). The forward primer contains a NheI site followed by the beginning of the open reading frame; the reverse primer contains the end of the open reading frame followed by a EcoRI cleavage site. PCR (1 min of denaturation at 95° C., 1 min of annealing at 55° C., and 1 min of elongation at 72° C.) was performed using pfu polymerase for 30 cycles with 25 pmol of each primer in a final volume of 50 µl. After electrophoresis on a 1% agarose gel, the amplified DNA, visible by ethidium bromide staining, was digested with NheI and EcoRI and cloned into NheI and EcoRI-digested pRSET plasmid vector to obtain the construct pRSET-A. The insert was sequenced to ascertain that no mutations had been introduced during amplification. The construct was used to transform *E. coli* JM109 (Invitrogen) for plasmid preparation and *E. coli* BL21(pLysS) for protein expression. The full-length *R. glutinis* cDNA in pBK-CMV expression vector containing T7lac promoter, which was then used to transform *E. coli* cells (JM109). Transformed bacteria were induced by treatment with IPTG to produce the recombinant protein. Protein extracts were prepared from the induced bacteria and assayed for ACP activity and found that there was an increase in ACP activity in JM109 cells transformed with the recombinant plasmid as compared to untransformed cells. SDS-polyacrylamide gel electrophoresis demonstrated that bacteria transformed with the recombinant plasmid contained a polypeptide of the expected size. Western blot analysis of the transformed JM109 cells with anti-ACP antibodies showed an intense signal at around 10 to 12 kDa and no signal was detected in the untransformed cells.

Expression of Recombinant *R. glutinis* ACP—Transformed BL21 cells were grown at 37° C. to an $A_{600}$ of 0.5 in LB medium (50 ml) containing 100 µg/ml ampicillin. A 10-ml portion was used to inoculate 1 liter fresh LB medium containing 100 µg/ml ampicillin, and the mixture was incubated overnight at 120 rpm at 37° C. Protein production was then induced by 0.5 mM IPTG. After a 3-h induction at 37° C., cells were harvested by centrifugation (10,000×g for 10 min at 4° C. The cells were harvested by centrifugation and then lysed by treating with lysozyme (0.1 mg/ml) at pH 8.0 (50 mM Tris-HCl) in the presence of 0.1% Triton X-100 for 20 min at 30° C. The mixture, cooled in ice, was sonicated two times for 10 s each using a probe sonicator (Branson). The sonicated mixture was centrifuged at 12,000×g for 10 min, and the supernatant was collected. This supernatant was used both to measure the ACP activity and for the affinity purification of the recombinant His-tagged enzyme.

Purification of Recombinant *R. glutinis* ACP—All steps were performed at 4° C. For the affinity purification of the recombinant enzyme, the bacterial extract (5 ml) in 20 mM Tris buffer (pH 8.0), 0.5 M NaCl and 5 mM imidazole was loaded onto a 2.5-ml nickel-nitrilotriacetic acid-agarose (Qiagen) column. The column was washed first with 10 volumes of the above binding buffer and further washed with six volumes of the same buffer but containing a higher concentration of imidazole (60 mM). The enzyme was eluted with six volumes of the buffer containing 0.3 M imidazole, followed by elution with four volumes of 1.0 M imidazole.

EXAMPLE XX

Cloning of diacylglycerol acyltransferase (DAG-AT)—cDNA library screening was performed using polyclonal antisera raised against peptide ID 5. To screen the expression library with antibody, plaques were grown for 4 h at 42° C. after plating and overlaid with IPTG soaked nitrocellulose membrane and incubated at 37° C. for 6–8 h. Membranes were developed by following the western blot procedure with primary antibody dilution 1:1000 in 0.5% gelatin in phosphate buffered saline containing 0.05% Tween 20. Three positive clones were sequenced as described above.

Expression of DAG-AT—The DAG-AT gene was transformed to *E. coli* JM109 cells independently and induced with 0.5 mM IPTG for 4 h. The crude cell lysate was sonicated and run in a 12% SDS-PAGE. Untransformed cell lysate was used as a control. The full-length *R. glutinis* cDNA in pBK-CMV expression vector containing T7lac promoter, which was then used to transform *E. coli* cells (JM109). Transformed bacteria were induced by treatment with IPTG to produce the recombinant protein. Protein extracts were prepared from the induced bacteria and assayed for DAG-At activity and found that there was a slight increase in DAG-AT activity in JM109 cells transformed with the recombinant plasmid as compared to untransformed cells.

TABLE I

Distribution of triacylglycerol biosynthetic enzyme activities in soluble and particulate fractions of R. glutinis

| Fraction | LPA acyltransferase Specific activity pmol/min/mg | LPA acyltransferase Total activity pmol/min | PA phosphatase Specific activity pmol/min/mg | PA phosphatase Total activity pmol/min | DAG acyltransferase Specific activity pmol/min/mg | DAG acyltransferase Total activity pmol/min |
|---|---|---|---|---|---|---|
| 10,000 × g Sup | 1.59 | 32.42 ± 4.54 | 1.14 | 27.35 ± 0.75 | 0.98 | 23.62 ± 1.65 |
| 240,000 × g Sup | 1.60 | 27.00 ± 3.78 | 1.16 | 19.5 ± 0.58 | 0.83 | 13.95 ± 1.12 |
| 240,000 × g Pellet | 1.88 | 12.29 ± 0.31 | 1.49 | 9.75 ± 0.20 | 1.96 | 14.75 ± 0.74 |

The logarithmic phase oleaginous yeast cells from 1 liter culture were lysed with glass bead and fractions were obtained by differential centrifugation. Enzyme activities were measured as described in Materials and Methods. Values are the mean ± SEM of nine separate experiments, each performed in duplicate.
Sup, supernatant.

TABLE II

Purification of triacylglycerol biosynthetic enzymes from oleaginous yeast

| Step | Protein μg | Specific activity pmol/min/mg | Total activity pmol/min | Yield % | Purification -fold |
|---|---|---|---|---|---|
| LPA acyltransferase | | | | | |
| Cytosol | 9500 | 1.57 | 14.92 | 100 | 1 |
| Native-PAGE | 11 | 736 | 8.10 | 56 | 469 |
| PA phosphatase | | | | | |
| Cytosol | 9500 | 1.29 | 12.26 | 100 | 1 |
| Native-PAGE | 11 | 550 | 6.25 | 51 | 426 |
| DAG acyltransferase | | | | | |
| Cytosol | 9500 | 0.96 | 9.12 | 100 | 1 |
| Native-PAGE | 11 | 393 | 3.56 | 39 | 409 |

TABLE III

TAG biosynthesizing capacity of the immunoprecipitate

| Antiserum used | LPA acyltransferase pmol/min | PA phosphatase pmol/min | DAG acyltransferase pmol/min |
|---|---|---|---|
| LPA acyltransferase | 1.52 ± 0.06 | 0.88 ± 0.03 | 0.48 ± 0.02 |
| PA phosphatase (major) | 1.38 ± 0.06 | 0.86 ± 0.04 | 0.42 ± 0.01 |
| PA phosphatase (minor) | 1.44 ± 0.04 | 0.84 ± 0.05 | 0.51 ± 0.06 |

TABLE IV

Distribution of TAG biosynthetic enzyme activities in the soluble and the particulate fractions of Hepg2, cold adapted liver and adipose tissues

| | LPA acyltransferase Cytosol | LPA acyltransferase Membranes | PA phosphatase Cytosol | PA phosphatase Membranes | DAG acyltransferase Cytosol | DAG acyltransferase Membranes |
|---|---|---|---|---|---|---|
| | (% Total activity, pmol/min/g tissue) | | | | | |
| HepG2 | 25 ± 2.1 | 75 ± 6.2 | 17 ± 1.5 | 83 ± 6.2 | 15 ± 0.9 | 85 ± 5.3 |
| Liver | 23 ± 1.3 | 77 ± 5.7 | 31 ± 2.6 | 69 ± 4.5 | 21 ± 1.1 | 79 ± 6.7 |
| BAT | 38 ± 1.8 | 62 ± 4.6 | 33 ± 1.4 | 67 ± 5.2 | 32 ± 2.3 | 68 ± 5.1 |
| WAT | 33 ± 2.3 | 67 ± 5.1 | 35 ± 2.7 | 65 ± 4.9 | 29 ± 1.8 | 71 ± 6.4 |

REFERENCES

1. Kennedy, E. P. (1961) Fed. Proc. Fed. Am. Soc. Exp. Biol. 20, 934–940
2. Bishop, W. R., and Bell R. M. (1988) Annu. Rev. Cell Biol. 4, 579–610
3. Kent, C., Carman, G. M., Spence, M. W., and Dowhan, W. (1991) FASEB. J. 5, 2258–2266
4. Raetz, C. R. H., and Dowhan, W. (1990) J. Biol. Chem. 265, 1235–1238
5. Webber, K. O., and Hajra, A. M. (1992) Methods Enzymol. 209, 92–98
6. Paltauf, F., Kholwein S. D., and Henry, S. A. (1992) in The molecular and cellular biology of the yeast *Saccharomyces* Vol. 2, pp. 415–500, Cold Spring Harbor Laboratory, New York
7. Athenstaedt, K., Weys, S., Paltauf, F., and Daum, G. (1999) J. Bacteriol. 181, 1458–1463
8. Pelech, S. L., and Vance, D. E. (1989) Trends Biochem. Sci. 14, 28–30.
9. Nishizuka, Y. (1986) Science 233, 305–312
10. Dahlqvist, A., Stahl, U., Lenman, M., Banas, A., Lee, M., Sandager, L., Ronne, H., and
11. Stymne, S. (2000) Proc. Natl. Acad. Sci. USA. 97, 6487–6492
12. Oelkers, P., Tinkelenberg, A., Erdeniz, N., Cromley, D., Billheimer, J. T., and Sturley, S. L. (2000) J. Biol. Chem. 275, 15609–15612
13. Stymne, S., and Stobart, A. K. (1987) in The biochemistry of plants (Stumpf, P. K., and Conn, E. E., eds), Vol. 9, pp. 175–214, Academic Press, New York
13. Somerville, C., and Browse, J. (1991) Science 252, 80–87
14. Zinser, E., Sperka-Gottlieb, C. D. M., Fasch, E-V., Kholwein, S. D., Paltauf, F., and Daum, G. (1991) J. Bacteriol. 173, 2026–2034
15. Suzuki, O. (1988) In Proceedings of the world conference on Biotechnology for the fats and oil industry (Applewhite, T. H., ed), pp. 110–116, American Oil Chemists' Society, Champaign
16. Weete, J. D. (1980) in Lipid biochemistry of fungi and other organisms, pp. 16–17, Plenum Press, New York
17. Bligh, E. G., and Dyer, W. J. (1959) Can. J. Biochem. Physiol. 31, 911–917
18. Green, N., Alexander, H., Olson, A., Alexander, S., Shinnick, T. M., Sutcliffe, J. G., and Lerner, R. A. (1982) Cell 28, 477–487
19. Engvall, E. (1980) Methods Enzymol. 70A, 419–439
20. Towbin, H., Staehelin, T., and Gordon, J. (1979) Proc. Natl. Acad. Sci. USA. 76, 4350–4354
21. Wakil, S. J., Stoops, J. K., and Joshi, V. C. (1983) Annu. Rev. Biochem. 52, 537–579
2. Rock, C. O., and Cronan, J. E. (1980) Anal. Biochem. 102, 362–364

The abbreviations used are: ACP, acyl carrier protein; DAG, diacylglycerol; G3P, glycerol-3-phosphate; LPA, lysophosphatidic acid; PA, phosphatidic acid; TAG, triacylglycerol; TBC, triacylglycerol biosynthetic complex, SOD, superoxide dismutase.

The invention claimed is:

1. An isolated phosphatidic acid phosphatase comprising a peptide having SEQ ID NO: 5.

2. An isolated phosphatidic acid phosphatase according to claim 1, said phosphatidic acid phosphatase being soluble in aqueous solutions.

* * * * *

SEQUENCE LISTING

```
<160> NUMBER OF SEQ ID NOS: 42

<210> SEQ ID NO 1
<211> LENGTH: 12
<212> TYPE: PRT
<213> ORGANISM: Artificial Sequence
<220> FEATURE:
<223> OTHER INFORMATION: Lysophosphatidic Acid Acyltransferase
<220> FEATURE:
<221> NAME/KEY: misc_feature
<222> LOCATION: (1)..(1)
<223> OTHER INFORMATION: Xaa can be any naturally occurring amino acid

<400> SEQUENCE: 1

Xaa Ala Leu Glu Leu Gln Ala Asp Asp Phe Asn Lys
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Lysophosphatidic Acid Acyltransferase

<400> SEQUENCE: 2

Ala Leu Glu Leu Gln Ala Asp Asp Phe Asn Lys
1               5                   10

<210> SEQ ID NO 3
<211> LENGTH: 13
<212> TYPE: PRT
<213> ORGANISM: Artificial Sequence
```

```
<220> FEATURE:
<223> OTHER INFORMATION: Lysophosphatidic Acid Acyltransferase
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 3

Xaa Xaa Val Asn Asn Val Xaa Pro Gly Xaa Ile Glu Gln
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Phosphatidic Acid Phosphatase

<400> SEQUENCE: 4

Asn Ala Leu Thr Gly Leu His Met Gly Gly Gly Lys
1               5                   10

<210> SEQ ID NO 5
<211> LENGTH: 9
<212> TYPE: PRT
<213> ORGANISM: Artificial Sequence
<220> FEATURE:
<223> OTHER INFORMATION: Phosphatidic Acid Phosphatase
<220> FEATURE:
<221> NAME/KEY: misc_feature
<222> LOCATION: (8)..(8)
<223> OTHER INFORMATION: Xaa can be any naturally occurring amino acid

<400> SEQUENCE: 5

Tyr Val Glu Gly Ala Arg Pro Xaa Lys
1               5

<210> SEQ ID NO 6
<211> LENGTH: 7
<212> TYPE: PRT
<213> ORGANISM: Artificial Sequence
<220> FEATURE:
<223> OTHER INFORMATION: Phosphatidic Acid Phosphatase

<400> SEQUENCE: 6

Tyr Val Glu Gly Ala Arg Pro
1               5

<210> SEQ ID NO 7
<211> LENGTH: 17
<212> TYPE: PRT
<213> ORGANISM: Artificial Sequence
<220> FEATURE:
<223> OTHER INFORMATION: Diacylglycerol Acyltransferase
<220> FEATURE:
<221> NAME/KEY: misc_feature
<222> LOCATION: (1)..(1)
<223> OTHER INFORMATION: Xaa can be any naturally occurring amino acid

<400> SEQUENCE: 7

Xaa Leu Trp Ala Val Val Gly Ala Gln Pro Phe Gly Gly Ala Arg Gly
1               5                   10                  15
```

-continued

Ser

<210> SEQ ID NO 8
<211> LENGTH: 20
<212> TYPE: PRT
<213> ORGANISM: Artificial Sequence
<220> FEATURE:
<223> OTHER INFORMATION: Acyl-Acyl Carrier Protein Synthetase

<400> SEQUENCE: 8

Val His Leu Ala Val Ala Leu Tyr Gly Leu Ala Ala Val Arg Val Ser
1               5                   10                  15

Arg Ile Val Arg
            20

<210> SEQ ID NO 9
<211> LENGTH: 732
<212> TYPE: DNA
<213> ORGANISM: Artificial Sequence
<220> FEATURE:
<223> OTHER INFORMATION: Superoxide Dismutase Gene Sequence

<400> SEQUENCE: 9
ggcaccaggg gcgacgactc gagccatggc cgcctataac aagatccctg ctgttctccc      60
gaagcttccc ttcgcgtaca acgctctgga gccggccatt tcctcccaga tcatggagct     120
ccaccactcg aagcaccacg ccacctacgt cgccaacttc aacaaggccc acgaggacat     180
ccaggctgct tcgcagggcc caggacatca agaagcagatt gccctccagg ccaccgtcaa     240
gttcaacggc ggtggccaca tcaaccacac cctcttctgg gagaacctcg cccccagtc      300 gcagggcggc ggccagttcc cctcgtcggg caagctccac gaccaagtcc agcaggactt     360
cggcggtctc gacggctttg aagaaggccg tcaacgccgc tgccctcggt atccagggat     420
ctggatgggc ctggctcggg gtacaacccg acgaccaaga accttgaggc tgtctcgacc     480
gcaaccaggg acccgcttct cggctacgtt ccccccgtcg gcatggacat gtgggagcac     540
gcttactaca tcgactacaa gaagtcaagg cctcgtacct cgaagtctct cggaggccta     600
agtctcgccc tcccttctcg agcccgcttg gaaggaagga aggaaaggaa tgcgcttgaa     660
cccatgtagt acgcgaaaag tcgaaatacg aaatcccctc agtcgttgca aaaaaaaaa      720 aaaaaaaaa aa                                                           732

<210> SEQ ID NO 10
<211> LENGTH: 565
<212> TYPE: DNA
<213> ORGANISM: Artificial Sequence
<220> FEATURE:
<223> OTHER INFORMATION: Acyl Carrier Protein Gene Sequence

<400> SEQUENCE: 10
ggcacgaggc tctctcacat cgtttgccgc tacatttcag cttaaagggt ctattcagct      60
cacgatgaag cacgtcgccg cctacctcct cctcgtctct gccggcaaca cctcgccctc     120
ggccgaggac gtcaagaagg tcctcgccgc cgccgacatc caggccgacg aggagcgcct     180
ctcggtcctc atcaaggagc tcgagggcaa ggacgtcaac gaggtcattg ccagggatc      240 caagaagctc gcttccgtcc cctcgggcgg cgccgcccc gccgctgccg ctggcggcgc      300
tgccgctggc ggtgccgccg aggagaaggc tgaggacaag cccgctgaga aggatgagga     360
gagcgacgac gacatgggct tcggtctctt cgactaagct ctcgtctcgc ctctcccct      420

```
ctgcgacgac gcacaacttt cccgaccttc ctcgacttgc cgaagcgttt catctctgta    480
gtttgggatc gatggattgc gctagggaag ccctgacgga aaggggggg tggtttggct    540 tctcaaaaaa aaaaaaaaaa aaaaa                                         565
```

<210> SEQ ID NO 11
<211> LENGTH: 1238
<212> TYPE: DNA
<213> ORGANISM: Artificial Sequence
<220> FEATURE:
<223> OTHER INFORMATION: Diacylglycerol Acyltransferase Gene Sequence

<400> SEQUENCE: 11

```
acactagtgg atccaaagaa ttcggcacga ggctcggctc tctcgcgtct ttacgtcccg     60
aagggtctgt gggagggcga gggcaagttc aaggagatcc ttctctccga ggttgccaag   120
atcactctcg gccccgtcac cgagttcgag cacttcatgg gtcccgtcat ctcgcaggct   180
tcgttcgaca gtgcctcag ctacgttgag aaggccaagc aggcaggtgg cgaggtcctc    240
gccggcggca agggcgacgc gtcgagcggt tactacgtcg agccgaccat catcctgacc   300
aaggaccctc gctcgcctac catggtcgac gagatcttcg gcccggtcct cactgtttac   360
atcttcgagg acgaccagta cgaggagacg tgcaagttga tcgaccagac gacgacgtac   420
gccctcactg gctgcatctt tcggacgac cgtgccgcga ctgtcaaggc cggtgctctc    480
ctccgccacg ctgcgggtaa ctactacatc aacgacaagt cgaccggtgc tgttgtcggt   540
gcccagcctt tcggtggcgc acgcggatcg ggcacgaacg acaaggcggg ctcgatgacg   600
ttcttcaccc gctggtgcca gccgcggagt gtgaaggaat ccttctgccc gcccgaatct   660
ttcccttacc cgtcgaacca gcgcgattaa atggaggagt tggggaggag gaggacgtcg   720
agggagctgg ggaggcggag gacgtcgagg aggagttggg gaggaggagg acgtcgaggg   780
agctggggag gcgaggacg tcgaggagga gttggggagg agtttgtcga ggaggaggag    840
aagggtttct cctcgcctgt agttgtacaa aatcagcacg cctttgcttc caccgccaaa   900
aaaaaaaaaa aaaaaaact cgagagtact tctagagcgg ccgcgggccc atcgattttc    960 caccccgggtg gggtaccagg taagtgtacc caattcgccc tatagtgagt cgtattacaa   1020
ttcactggcc gtcgttttac aacgtcgtga ctgggaaaac cctggcgtta cccaacttaa   1080
tcgccttgca gcacatcccc ctttcgccag ctggcgtaat agcgaagagg cccggaccga   1140
tcgcccttcc aacagttgcg cagcctgatg gcgaatggag atccaatttt taagtgtata   1200 agggtaaac tactgatcta attgtggggt ttttaaat                            1238
```

<210> SEQ ID NO 12
<211> LENGTH: 20
<212> TYPE: PRT
<213> ORGANISM: Artificial Sequence
<220> FEATURE:
<223> OTHER INFORMATION: Superoxide dismutase

<400> SEQUENCE: 12

```
Ala Tyr Asn Lys Ile Pro Ala Val Ala Leu Pro Lys Leu Pro Phe Ala
1               5                   10                  15

Thr Asn Ala Leu
            20
```

<210> SEQ ID NO 13
<211> LENGTH: 45
<212> TYPE: DNA
<213> ORGANISM: Artificial Sequence

```
<220> FEATURE:
<223> OTHER INFORMATION: Superoxide dismutase primer
<220> FEATURE:
<221> NAME/KEY: misc_feature
<222> LOCATION: (15)..(15)
<223> OTHER INFORMATION: n = inosine
<220> FEATURE:
<221> NAME/KEY: misc_feature
<222> LOCATION: (18)..(18)
<223> OTHER INFORMATION: n = inosine
<220> FEATURE:
<221> NAME/KEY: misc_feature
<222> LOCATION: (33)..(33)
<223> OTHER INFORMATION: n = inosine
<220> FEATURE:
<221> NAME/KEY: misc_feature
<222> LOCATION: (39)..(39)
<223> OTHER INFORMATION: n = inosine

<400> SEQUENCE: 13
tacaacaaga tcccngtnct ccctaagctc ccnttcgcnt acaac            45

<210> SEQ ID NO 14
<211> LENGTH: 34
<212> TYPE: DNA
<213> ORGANISM: Artificial Sequence
<220> FEATURE:
<223> OTHER INFORMATION: Acyl carrier protein forward primer

<400> SEQUENCE: 14
cgaagctagc atgaagcacg tcgccgccta cctc                        34

<210> SEQ ID NO 15
<211> LENGTH: 32
<212> TYPE: DNA
<213> ORGANISM: Artificial Sequence
<220> FEATURE:
<223> OTHER INFORMATION: Acyl carrier protein reverse primer

<400> SEQUENCE: 15
gcgaattctt agtcgaagag accgaagccc at                          32

<210> SEQ ID NO 16
<211> LENGTH: 191
<212> TYPE: PRT
<213> ORGANISM: Artificial Sequence
<220> FEATURE:
<223> OTHER INFORMATION: Superoxide Dismutase Protein Sequence

<400> SEQUENCE: 16

Met Ala Ala Tyr Asn Lys Ile Pro Ala Val Leu Pro Lys Leu Pro Phe
1               5                   10                  15

Ala Tyr Asn Ala Leu Glu Pro Ala Ile Ser Ser Gln Ile Met Glu Leu
            20                  25                  30

His His Ser Lys His His Ala Thr Tyr Val Ala Asn Phe Asn Lys Ala
        35                  40                  45

His Glu Asp Ile Gln Ala Ala Ser Gln Ala Gln Asp Ile Lys Lys Gln
    50                  55                  60

Ile Ala Leu Gln Ala Thr Val Lys Phe Asn Gly Gly His Ile Asn
65                  70                  75                  80

His Thr Leu Phe Trp Glu Asn Leu Ala Pro Gln Ser Gln Gly Gly Gly
                85                  90                  95

Gln Phe Pro Ser Ser Gly Lys Leu His Asp Gln Val Gln Gln Asp Phe
            100                 105                 110

Gly Gly Leu Asp Gly Phe Glu Glu Gly Arg Gln Arg Arg Cys Pro Arg
```

```
                    115                 120                 125
Tyr Pro Gly Ile Trp Met Gly Leu Ala Arg Gly Thr Thr Arg Pro
            130                 135                 140

Arg Thr Leu Arg Leu Ser Arg Pro Gln Pro Gly Thr Arg Phe Ser Ala
145                 150                 155                 160

Thr Phe Pro Pro Ser Ala Trp Thr Cys Gly Ser Thr Leu Thr Thr Ser
                165                 170                 175

Thr Thr Arg Ser Gln Gly Leu Val Pro Arg Ser Leu Ser Glu Ala
            180                 185                 190

<210> SEQ ID NO 17
<211> LENGTH: 110
<212> TYPE: PRT
<213> ORGANISM: Artificial Sequence
<220> FEATURE:
<223> OTHER INFORMATION: Acyl Carrier Protein Sequence

<400> SEQUENCE: 17

Met Lys His Val Ala Ala Tyr Leu Leu Leu Val Ser Ala Gly Asn Thr
1               5                   10                  15

Ser Pro Ser Ala Glu Asp Val Lys Lys Val Leu Ala Ala Ala Asp Ile
            20                  25                  30

Gln Ala Asp Glu Glu Arg Leu Ser Val Leu Ile Lys Glu Leu Glu Gly
        35                  40                  45

Lys Asp Val Asn Glu Val Ile Ala Glu Gly Ser Lys Lys Leu Ala Ser
    50                  55                  60

Val Pro Ser Gly Gly Ala Ala Pro Ala Ala Ala Gly Gly Ala Ala
65                  70                  75                  80

Ala Gly Gly Ala Ala Glu Glu Lys Ala Glu Asp Lys Pro Ala Glu Lys
                85                  90                  95

Asp Glu Glu Ser Asp Asp Asp Met Gly Phe Gly Leu Phe Asp
            100                 105                 110

<210> SEQ ID NO 18
<211> LENGTH: 211
<212> TYPE: PRT
<213> ORGANISM: Artificial Sequence
<220> FEATURE:
<223> OTHER INFORMATION: Diacylglycerol  Acyltransferase Protein
      Sequence

<400> SEQUENCE: 18

Thr Leu Val Asp Pro Lys Asn Ser Ala Arg Gly Ser Ala Leu Ser Arg
1               5                   10                  15

Leu Tyr Val Pro Lys Gly Leu Trp Glu Gly Glu Gly Lys Phe Lys Glu
            20                  25                  30

Ile Leu Leu Ser Glu Val Ala Lys Ile Thr Leu Gly Pro Val Thr Glu
        35                  40                  45

Phe Glu His Phe Met Gly Pro Val Ile Ser Gln Ala Ser Phe Asp Lys
    50                  55                  60

Cys Leu Ser Tyr Val Glu Lys Ala Lys Gln Ala Gly Gly Glu Val Leu
65                  70                  75                  80

Ala Gly Gly Lys Gly Asp Ala Ser Ser Gly Tyr Tyr Val Glu Pro Thr
                85                  90                  95

Ile Ile Leu Thr Lys Asp Pro Arg Ser Pro Thr Met Val Asp Glu Ile
            100                 105                 110

Lys Gly Pro Val Leu Thr Val Tyr Ile Phe Glu Asp Asp Gln Tyr Glu
            115                 120                 125
```

-continued

Glu Thr Cys Lys Leu Ile Asp Gln Thr Thr Thr Tyr Ala Leu Thr Gly
    130                 135                 140

Cys Ile Phe Ser Asp Asp Arg Ala Ala Thr Val Lys Ala Gly Ala Leu
145                 150                 155                 160

Leu Arg His Ala Ala Gly Asn Tyr Tyr Ile Asn Asp Lys Ser Thr Gly
                165                 170                 175

Ala Val Val Gly Ala Gln Pro Phe Gly Gly Ala Arg Gly Ser Gly Thr
            180                 185                 190

Asn Asp Lys Ala Gly Ser Met Thr Phe Phe Thr Arg Trp Cys Gln Pro
        195                 200                 205

Arg Ser Val
    210

<210> SEQ ID NO 19
<211> LENGTH: 222
<212> TYPE: PRT
<213> ORGANISM: Homo sapiens

<400> SEQUENCE: 19

Met Leu Ser Arg Ala Val Cys Gly Thr Ser Arg Gln Leu Ala Pro Ala
1               5                   10                  15

Leu Gly Val Leu Gly Ser Arg Gln Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Ala Tyr Val Asn Asn Leu Asn Val
    50                  55                  60

Thr Glu Glu Lys Tyr Gln Glu Ala Leu Ala Lys Gly Asp Val Thr Ala
65                  70                  75                  80

Gln Ile Ala Leu Gln Pro Ala Leu Lys Phe Asn Gly Gly Gly His Ile
                85                  90                  95

Asn His Ala Ile Phe Trp Thr Asn Leu Ser Pro Asn Gly Gly Gly Glu
            100                 105                 110

Pro Lys Gly Glu Leu Leu Glu Ala Ile Lys Arg Asp Phe Gly Ser Phe
        115                 120                 125

Asp Lys Phe Lys Glu Lys Leu Thr Ala Ala Ser Val Gly Val Gln Gly
    130                 135                 140

Ser Gly Trp Gly Trp Leu Gly Phe Asn Lys Glu Arg Gly His Leu Gln
145                 150                 155                 160

Ile Ala Ala Cys Pro Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Glu Arg Tyr Met Ala Cys Lys Lys
    210                 215                 220

<210> SEQ ID NO 20
<211> LENGTH: 222
<212> TYPE: PRT
<213> ORGANISM: Bos taurus

<400> SEQUENCE: 20

Met Leu Ser Arg Ala Ala Cys Ser Thr Ser Arg Arg Leu Val Pro Ala
1               5                   10                  15

-continued

Leu Ser Val Leu Gly Ser Arg Gln Lys His Ser Leu Pro Asp Leu Pro
                20                  25                  30

Tyr Asp Tyr Gly Ala Leu Glu Pro His Ile Asn Ala Gln Ile Met Gln
            35                  40                  45

Leu His His Ser Lys His His Ala Ala Tyr Val Asn Asn Leu Asn Val
        50                  55                  60

Ala Glu Glu Lys Tyr Arg Glu Ala Leu Glu Lys Gly Asp Val Thr Ala
65                  70                  75                  80

Gln Ile Ala Leu Gln Pro Ala Leu Lys Phe Asn Gly Gly His Ile
                85                  90                  95

Asn His Ser Ile Phe Trp Thr Asn Leu Ser Pro Asn Gly Gly Glu
            100                 105                 110

Pro Gln Gly Glu Leu Leu Glu Ala Ile Lys Arg Asp Phe Gly Ser Phe
        115                 120                 125

Ala Lys Phe Lys Glu Lys Leu Thr Ala Val Ser Val Gly Val Gln Gly
130                 135                 140

Ser Gly Trp Gly Trp Leu Gly Phe Asn Lys Glu Gln Gly Arg Leu Gln
145                 150                 155                 160

Ile Ala Ala Cys Ser Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Thr Ala Arg Tyr Thr Ala Cys Ser Lys
210                 215                 220

<210> SEQ ID NO 21
<211> LENGTH: 202
<212> TYPE: PRT
<213> ORGANISM: Oryctolagus cuniculus

<400> SEQUENCE: 21

His Gly Arg Gly Met Lys His Ser Leu Pro Asp Leu Pro Tyr Asp Tyr
1               5                   10                  15

Gly Ala Leu Glu Pro His Ile Asn Ala Gln Ile Met Glu Leu His His
                20                  25                  30

Ser Lys His His Ala Ala Tyr Val Asn Asn Leu Asn Ala Thr Glu Glu
            35                  40                  45

Lys Tyr Arg Glu Ala Leu Ala Arg Gly Asp Val Thr Ala His Val Ala
        50                  55                  60

Leu Gln Pro Ala Leu Lys Phe Lys Gly Gly His Ile Asn His Thr
65                  70                  75                  80

Ile Phe Trp Thr Asn Leu Ser Pro Asn Gly Gly Glu Pro Lys Gly
                85                  90                  95

Glu Leu Leu Glu Ala Ile Lys Arg Asp Phe Gly Ser Phe Asp Lys Phe
            100                 105                 110

Lys Glu Arg Leu Thr Ala Val Ser Val Gly Val Gln Gly Ser Gly Trp
        115                 120                 125

Gly Trp Leu Gly Phe Asn Lys Glu Gln Gly His Leu Gln Ile Ala Ala
130                 135                 140

Cys Ala Asn Gln Asp Pro Leu Gln Gly Thr Thr Gly Leu Ile Pro Leu
145                 150                 155                 160

Leu Gly Ile Asp Val Trp Glu His Ala Tyr Tyr Leu Gln Tyr Lys Asn

```
                    165                 170                 175
Val Arg Pro Asp Tyr Leu Lys Ala Ile Trp Asn Val Ile Thr Trp Glu
            180                 185                 190

Asn Val Thr Glu Arg Tyr Met Ala Cys Lys
        195                 200

<210> SEQ ID NO 22
<211> LENGTH: 222
<212> TYPE: PRT
<213> ORGANISM: Rattus rattus

<400> SEQUENCE: 22

Met Leu Cys Arg Ala Ala Cys Ser Ala Gly Arg Arg Leu Gly Pro Ala
1               5                   10                  15

Ala Ser Thr Ala Gly Ser Arg His Lys His Ser Leu Pro Asp Leu Pro
            20                  25                  30

Tyr Asp Tyr Gly Ala Leu Glu Pro His Ile Asn Ala Gln Ile Met Gln
        35                  40                  45

Leu His His Ser Lys His His Ala Thr Tyr Val Asn Asn Leu Asn Val
    50                  55                  60

Thr Glu Glu Lys Tyr His Glu Ala Leu Ala Lys Gly Asp Val Thr Thr
65                  70                  75                  80

Gln Val Ala Leu Gln Pro Ala Leu Lys Phe Asn Gly Gly Gly His Ile
                85                  90                  95

Asn His Ser Ile Phe Trp Thr Asn Leu Ser Pro Lys Gly Gly Gly Glu
            100                 105                 110

Pro Lys Gly Glu Leu Leu Glu Ala Ile Lys Arg Asp Phe Gly Ser Phe
        115                 120                 125

Glu Lys Phe Lys Glu Lys Leu Thr Ala Val Ser Val Gly Val Gln Gly
    130                 135                 140

Ser Gly Trp Gly Trp Leu Gly Phe Asn Lys Glu Gln Gly Arg Leu Gln
145                 150                 155                 160

Ile Ala Ala Cys Ser Asn Gln Asp Pro Leu Gln Gly Thr Thr Gly Leu
                165                 170                 175

Ile Pro Leu Leu Gly Ile Asp Val Trp Glu His Ala Tyr Tyr Leu Gln
            180                 185                 190

Tyr Lys Asn Val Arg Pro Asp Tyr Leu Lys Ala Ile Trp Asn Val Ile
        195                 200                 205

Asn Trp Glu Asn Val Ser Gln Arg Tyr Ile Val Cys Lys Lys
    210                 215                 220

<210> SEQ ID NO 23
<211> LENGTH: 193
<212> TYPE: PRT
<213> ORGANISM: Escherichia coli

<400> SEQUENCE: 23

Met Ser Phe Glu Leu Pro Ala Leu Pro Tyr Ala Lys Asp Ala Leu Ala
1               5                   10                  15

Pro His Ile Ser Ala Glu Thr Ile Glu Tyr His Tyr Gly Lys His His
            20                  25                  30

Gln Thr Tyr Val Thr Asn Leu Asn Asn Leu Ile Lys Gly Thr Ala Phe
        35                  40                  45

Glu Gly Lys Ser Leu Glu Glu Ile Ile Arg Ser Ser Glu Gly Gly Val
    50                  55                  60

Phe Asn Asn Ala Ala Gln Val Trp Asn His Thr Phe Tyr Trp Asn Cys
```

```
            65                  70                  75                  80
Leu Ala Pro Asn Ala Gly Gly Glu Pro Thr Gly Lys Val Ala Glu Ala
                85                  90                  95
Ile Ala Ala Ser Phe Gly Ser Phe Ala Asp Phe Lys Ala Gln Phe Thr
            100                 105                 110
Asp Ala Ala Ile Lys Asn Phe Gly Ser Gly Trp Thr Trp Leu Val Lys
            115                 120                 125
Asn Ser Asp Gly Lys Leu Ala Ile Val Ser Thr Ser Asn Ala Gly Thr
            130                 135                 140
Pro Leu Thr Thr Asp Ala Thr Pro Leu Leu Thr Val Asp Val Trp Glu
145                 150                 155                 160
His Ala Tyr Tyr Ile Asp Tyr Arg Asn Ala Arg Pro Gly Tyr Leu Glu
                165                 170                 175
His Phe Trp Ala Leu Val Asn Trp Glu Phe Val Ala Lys Asn Leu Ala
            180                 185                 190
Ala

<210> SEQ ID NO 24
<211> LENGTH: 233
<212> TYPE: PRT
<213> ORGANISM: Pisum sativum

<400> SEQUENCE: 24

Met Ala Ala Arg Thr Leu Leu Cys Arg Lys Thr Leu Ser Ser Val Leu
1               5                   10                  15
Arg Asn Asp Ala Lys Pro Ile Gly Ala Ala Ile Ala Ala Ala Ser Thr
            20                  25                  30
Gln Ser Arg Gly Leu His Val Phe Thr Leu Pro Asp Leu Ala Tyr Asp
        35                  40                  45
Tyr Gly Ala Leu Glu Pro Val Ile Ser Gly Glu Ile Met Gln Ile His
    50                  55                  60
His Gln Lys His His Gln Thr Tyr Ile Thr Asn Tyr Asn Lys Ala Leu
65                  70                  75                  80
Glu Gln Leu His Asp Ala Val Ala Lys Ala Asp Thr Ser Thr Thr Val
                85                  90                  95
Lys Leu Gln Asn Ala Ile Lys Phe Asn Gly Gly Gly His Ile Asn His
            100                 105                 110
Ser Ile Phe Trp Lys Asn Leu Ala Pro Val Ser Glu Gly Gly Gly Glu
            115                 120                 125
Pro Pro Lys Glu Ser Leu Gly Trp Ala Ile Asp Thr Asn Phe Gly Ser
            130                 135                 140
Leu Glu Ala Leu Ile Gln Lys Ile Asn Ala Glu Gly Ala Ala Leu Gln
145                 150                 155                 160
Trp Leu Gly Leu Asp Lys Asp Leu Lys Arg Leu Val Val Glu Thr Thr
                165                 170                 175
Gln Asp Pro Leu Val Thr Lys Gly Ala Ser Leu Val Pro Leu Leu Gly
            180                 185                 190
Ile Asp Val Trp Glu His Ala Tyr Tyr Leu Gln Tyr Lys Asn Val Arg
            195                 200                 205
Pro Asp Tyr Leu Lys Asn Ile Trp Lys Val Ile Asn Trp Lys His Ala
            210                 215                 220
Ser Glu Val Tyr Glu Lys Glu Ser Ser
225                 230
```

```
<210> SEQ ID NO 25
<211> LENGTH: 228
<212> TYPE: PRT
<213> ORGANISM: Capsicum annuum

<400> SEQUENCE: 25

Met Ala Leu Arg Asn Leu Met Thr Lys Lys Pro Phe Ala Gly Ile Leu
1               5                   10                  15

Thr Phe Arg Gln Gln Leu Arg Cys Val Gln Thr Phe Ser Leu Pro Asp
            20                  25                  30

Leu Ser Tyr Asp Tyr Gly Ala Leu Glu Pro Ala Ile Ser Gly Glu Ile
        35                  40                  45

Met Gln Leu His His Gln Lys His His Gln Thr Tyr Ile Thr Asn Tyr
    50                  55                  60

Asn Asn Ala Leu Gln Gln Leu His Asp Ala Ile Asn Lys Gly Asp Ser
65                  70                  75                  80

Pro Thr Val Ala Lys Leu Gln Gly Ala Ile Lys Phe Asn Gly Gly Gly
                85                  90                  95

His Ile Asn His Ser Val Phe Trp Lys Asn Leu Ala Pro Thr Arg Glu
            100                 105                 110

Gly Gly Gly Glu Pro Pro Lys Gly Ser Leu Gly Ser Ala Ile Asp Thr
        115                 120                 125

Asn Phe Gly Ser Leu Glu Ala Val Ile Gln Lys Met Asn Ala Glu Gly
    130                 135                 140

Ala Ala Leu Gln Gly Ser Gly Trp Val Trp Leu Gly Leu Asp Lys Glu
145                 150                 155                 160

Leu Lys Arg Leu Val Ile Glu Thr Thr Ala Asn Gln Asp Pro Leu Val
                165                 170                 175

Ile Lys Gly Pro Asn Leu Val Pro Leu Leu Gly Ile Asp Val Trp Glu
            180                 185                 190

His Ala Tyr Tyr Leu Gln Tyr Lys Asn Val Lys Pro Asp Tyr Leu Lys
        195                 200                 205

Asn Ile Trp Lys Val Ile Asn Trp Lys Tyr Ala Ala Glu Val Tyr Glu
    210                 215                 220

Lys Glu Cys Pro
225

<210> SEQ ID NO 26
<211> LENGTH: 235
<212> TYPE: PRT
<213> ORGANISM: Zea mays

<400> SEQUENCE: 26

Met Ala Leu Arg Thr Leu Ala Ser Lys Lys Val Leu Ser Phe Pro Phe
1               5                   10                  15

Gly Gly Ala Gly Arg Pro Leu Ala Ala Ala Ser Ala Arg Gly Val
            20                  25                  30

Thr Thr Val Thr Leu Pro Asp Leu Ser Tyr Asp Phe Gly Ala Leu Glu
        35                  40                  45

Pro Ala Ile Ser Gly Glu Ile Met Arg Leu His His Gln Lys His His
    50                  55                  60

Ala Thr Tyr Val Ala Asn Tyr Asn Lys Ala Leu Glu Gln Leu Glu Thr
65                  70                  75                  80

Ala Val Ser Lys Gly Asp Ala Ser Ala Val Val Gln Leu Gln Ala Ala
                85                  90                  95

Ile Lys Phe Asn Gly Gly Gly His Val Asn His Ser Ile Phe Trp Lys
```

```
                        100                 105                 110
Asn Leu Lys Pro Ile Ser Glu Gly Gly Glu Pro Pro His Gly Lys
            115                 120                 125

Leu Gly Trp Ala Ile Asp Glu Asp Phe Gly Ser Phe Glu Ala Leu Val
130                 135                 140

Lys Lys Met Asn Ala Glu Gly Ala Ala Leu Gln Gly Ser Gly Trp Val
145                 150                 155                 160

Trp Leu Ala Leu Asp Lys Glu Ala Lys Lys Val Ser Val Glu Thr Thr
                165                 170                 175

Ala Asn Gln Asp Pro Leu Val Thr Lys Gly Ala Ser Leu Val Pro Leu
            180                 185                 190

Leu Gly Ile Asp Val Trp Glu His Ala Tyr Tyr Leu Gln Tyr Lys Asn
                195                 200                 205

Val Arg Pro Asp Tyr Leu Asn Asn Ile Trp Lys Val Met Asn Trp Lys
            210                 215                 220

Tyr Ala Gly Glu Val Tyr Glu Asn Val Leu Ala
225                 230                 235

<210> SEQ ID NO 27
<211> LENGTH: 200
<212> TYPE: PRT
<213> ORGANISM: Ganoderma microsporum

<400> SEQUENCE: 27

Met Ala His Val Leu Pro Asp Leu Pro Tyr Ala Tyr Asn Ala Leu Glu
1               5                   10                  15

Pro Phe Ile Ser Gln Gln Ile Met Glu Leu His His Lys His His
            20                  25                  30

Gln Thr Tyr Val Asn Ser Leu Asn Ala Ala Glu Gln Ala Tyr Ala Lys
            35                  40                  45

Ala Ser Thr Pro Lys Glu Arg Ile Ala Leu Gln Ser Ala Leu Lys Phe
        50                  55                  60

Asn Gly Gly His Ile Asn His Ser Leu Phe Trp Lys Asn Leu Ala
65              70                  75                  80

Pro Ala Lys Ser Glu Gly Lys Gly Asn Gly Gly Ala Leu Ala Asp Gly
                85                  90                  95

Pro Leu Lys Ser Ala Ile Glu Gln Asn Trp Gly Ser Val Asp Asn Phe
            100                 105                 110

Ile Lys Glu Phe Asn Ala Thr Thr Ala Ala Ile Gln Gly Ser Gly Trp
            115                 120                 125

Gly Trp Leu Gly Leu Asn Pro Ala Thr Lys Arg Leu Glu Ile Thr Thr
130                 135                 140

Thr Ala Asn Gln Asp Pro Leu Leu Ser His Val Pro Ile Ile Gly Val
145                 150                 155                 160

Asp Ile Trp Glu His Ala Phe Tyr Leu Gln Tyr Leu Asn Val Lys Ala
                165                 170                 175

Asp Tyr Leu Ala Ala Ile Trp Ile Val Ile Asn Phe Lys Glu Ala Glu
            180                 185                 190

Arg Arg Leu Ile Glu Ala Thr Lys
        195                 200

<210> SEQ ID NO 28
<211> LENGTH: 233
<212> TYPE: PRT
<213> ORGANISM: Saccharomyces cerevisiae
```

<400> SEQUENCE: 28

| | | | | | | | | | | | | | | |
|---|---|---|---|---|---|---|---|---|---|---|---|---|---|---|
|Met|Phe|Ala|Lys|Thr|Ala|Ala|Asn|Leu|Thr|Lys|Lys|Gly|Gly|Leu|
|1| | | |5| | | | |10| | | | |15|

Ser Leu Leu Ser Thr Thr Ala Arg Arg Thr Lys Val Thr Leu Pro Asp
                20                  25                  30

Leu Lys Trp Asp Phe Gly Ala Leu Glu Pro Tyr Ile Ser Gly Gln Ile
            35                  40                  45

Asn Glu Leu His Tyr Thr Lys His His Gln Thr Tyr Val Asn Gly Phe
        50                  55                  60

Asn Thr Ala Val Asp Gln Phe Gln Glu Leu Ser Asp Leu Leu Ala Lys
65                  70                  75                  80

Glu Pro Ser Pro Ala Asn Ala Arg Lys Met Ile Ala Ile Gln Gln Asn
                85                  90                  95

Ile Lys Phe His Gly Gly Gly Phe Thr Asn His Cys Leu Phe Trp Glu
                100                 105                 110

Asn Leu Ala Pro Glu Ser Gln Gly Gly Gly Pro Pro Thr Gly Ala
            115                 120                 125

Leu Ala Lys Ala Ile Asp Glu Gln Phe Gly Ser Leu Asp Glu Leu Ile
        130                 135                 140

Lys Leu Thr Asn Thr Lys Leu Ala Gly Val Gln Gly Ser Gly Trp Ala
145                 150                 155                 160

Phe Ile Val Lys Asn Leu Ser Asn Gly Gly Lys Leu Asp Val Val Gln
                165                 170                 175

Thr Tyr Asn Gln Asp Thr Val Thr Gly Pro Leu Val Pro Leu Val Ala
            180                 185                 190

Ile Asp Ala Trp Glu His Ala Tyr Tyr Leu Gln Tyr Gln Asn Lys Lys
        195                 200                 205

Ala Asp Tyr Phe Lys Ala Ile Trp Asn Val Val Asn Trp Lys Glu Ala
    210                 215                 220

Ser Arg Arg Phe Asp Ala Gly Lys Ile
225                 230

<210> SEQ ID NO 29
<211> LENGTH: 191
<212> TYPE: PRT
<213> ORGANISM: Rhodotorula glutinis

<400> SEQUENCE: 29

Met Ala Ala Tyr Asn Lys Ile Pro Ala Val Leu Pro Lys Leu Pro Phe
1               5                   10                  15

Ala Tyr Asn Ala Leu Glu Pro Ala Ile Ser Ser Gln Ile Met Glu Leu
                20                  25                  30

His His Ser Lys His His Ala Thr Tyr Val Ala Asn Phe Asn Lys Ala
            35                  40                  45

His Glu Asp Ile Gln Ala Ala Ser Gln Ala Gln Asp Ile Lys Lys Gln
        50                  55                  60

Ile Ala Leu Gln Ala Thr Val Lys Phe Asn Gly Gly His Ile Asn
65                  70                  75                  80

His Thr Leu Phe Trp Glu Asn Leu Ala Pro Gln Ser Gln Gly Gly Gly
                85                  90                  95

Gln Phe Pro Ser Ser Gly Lys Leu His Asp Val Gln Gln Asp Phe
            100                 105                 110

Gly Gly Leu Asp Gly Phe Glu Glu Gly Arg Gln Arg Arg Cys Pro Arg
        115                 120                 125

```
Tyr Pro Gly Ile Trp Met Gly Leu Ala Arg Gly Thr Thr Arg Arg Pro
            130                 135                 140
Arg Thr Leu Arg Leu Ser Arg Pro Gln Pro Gly Thr Arg Phe Ser Ala
145                 150                 155                 160
Thr Phe Pro Arg Ser Ala Leu Thr Cys Gly Ser Thr Leu Thr Thr Ser
                165                 170                 175
Thr Thr Arg Ser Gln Gly Leu Val Pro Arg Ser Leu Ser Glu Ala
            180                 185                 190
```

<210> SEQ ID NO 30
<211> LENGTH: 111
<212> TYPE: PRT
<213> ORGANISM: Cladosporium sp.

<400> SEQUENCE: 30

```
Met Lys Tyr Met Ala Ala Tyr Leu Leu Leu Gly Leu Ala Gly Asn Ser
1               5                   10                  15
Ser Pro Ser Ala Glu Asp Ile Lys Thr Val Leu Ser Ser Val Gly Ile
            20                  25                  30
Asp Ala Asp Glu Glu Arg Leu Ser Ser Leu Leu Lys Glu Leu Glu Gly
        35                  40                  45
Lys Asp Ile Asn Glu Leu Ile Ser Ser Gly Ser Gln Lys Leu Ala Ser
    50                  55                  60
Val Pro Ser Gly Gly Ser Gly Ala Ala Pro Ser Ala Gly Gly Ala Ala
65                  70                  75                  80
Ala Ala Gly Gly Ala Thr Glu Ala Ala Pro Glu Ala Ala Lys Glu Glu
                85                  90                  95
Glu Lys Glu Glu Ser Asp Asp Asp Met Gly Phe Gly Leu Phe Asp
            100                 105                 110
```

<210> SEQ ID NO 31
<211> LENGTH: 113
<212> TYPE: PRT
<213> ORGANISM: Alternaria alternata

<400> SEQUENCE: 31

```
Met Lys His Leu Ala Ala Tyr Leu Leu Leu Gly Leu Gly Gly Asn Thr
1               5                   10                  15
Ser Pro Ser Ala Ala Asp Val Lys Ala Val Leu Glu Ser Val Gly Ile
            20                  25                  30
Glu Ala Asp Ser Asp Arg Leu Asp Lys Leu Ile Ser Glu Leu Glu Gly
        35                  40                  45
Lys Asp Ile Asn Glu Leu Ile Ala Ser Gly Ser Glu Lys Leu Ala Ser
    50                  55                  60
Val Pro Ser Gly Gly Ala Gly Gly Ala Ala Ser Gly Gly Ala Ala
65                  70                  75                  80
Ala Ala Gly Gly Ser Ala Gln Ala Glu Ala Pro Glu Ala Ala Lys
                85                  90                  95
Glu Glu Glu Lys Glu Glu Ser Asp Glu Asp Met Gly Phe Gly Leu Phe
            100                 105                 110
Asp
```

<210> SEQ ID NO 32
<211> LENGTH: 110
<212> TYPE: PRT
<213> ORGANISM: Schizosaccharomyces pombe

<400> SEQUENCE: 32

```
Met Lys Tyr Leu Ala Ala Tyr Leu Leu Thr Val Gly Gly Lys Asp
1               5                   10                  15

Ser Pro Ser Ala Ser Asp Ile Glu Ser Val Leu Ser Thr Val Gly Ile
            20                  25                  30

Glu Ala Glu Ser Glu Arg Ile Glu Thr Leu Ile Asn Glu Leu Asn Gly
                35                  40                  45

Lys Asp Ile Asp Glu Leu Ile Ala Ala Gly Asn Glu Lys Leu Ala Thr
    50                  55                  60

Val Pro Thr Gly Gly Ala Ala Ser Ala Pro Ala Ala Ala Gly
65                  70                  75              80

Gly Ala Ala Pro Ala Ala Glu Glu Ala Ala Lys Glu Ala Lys Glu
                85                  90                  95

Glu Glu Glu Ser Asp Glu Asp Met Gly Phe Gly Leu Phe Asp
                100                 105                 110

<210> SEQ ID NO 33
<211> LENGTH: 113
<212> TYPE: PRT
<213> ORGANISM: Zea mays

<400> SEQUENCE: 33

Met Lys Val Ile Ala Ala Tyr Leu Leu Ala Val Leu Gly Gly Asn Thr
1               5                   10                  15

Ser Pro Thr Ala Asp Asp Val Lys Ser Ile Leu Glu Ser Val Gly Ala
            20                  25                  30

Glu Ala Asp Glu Glu Lys Leu Glu Phe Leu Leu Thr Glu Leu Lys Asp
                35                  40                  45

Lys Asp Ile Thr Glu Val Ile Ala Ala Gly Arg Glu Arg Leu Ser Ser
    50                  55                  60

Val Pro Ser Gly Gly Ala Ile Asp Met Gly Ala Pro Ala Ala Val
65                  70                  75              80

Ala Gly Gly Ala Ala Pro Ala Glu Glu Ala Lys Lys Glu Glu Lys
                85                  90                  95

Val Glu Glu Lys Glu Glu Ser Asp Glu Asp Met Gly Phe Ser Leu Phe
                100                 105                 110

Asp

<210> SEQ ID NO 34
<211> LENGTH: 115
<212> TYPE: PRT
<213> ORGANISM: Rattus rattus

<400> SEQUENCE: 34

Met Arg Tyr Val Ala Ser Tyr Leu Leu Ala Ala Leu Gly Gly Asn Ser
1               5                   10                  15

Asn Pro Ser Ala Lys Asp Ile Lys Lys Ile Leu Asp Ser Val Gly Ile
            20                  25                  30

Glu Ala Asp Asp Glu Arg Leu Asn Lys Val Ile Ser Glu Leu Asn Gly
                35                  40                  45

Lys Asn Ile Glu Asp Val Ile Ala Gln Gly Val Gly Lys Leu Ala Ser
    50                  55                  60

Val Pro Ala Gly Gly Val Ala Val Ser Ala Pro Gly Ser Ala
65                  70                  75              80

Ala Pro Ala Ala Gly Ser Ala Pro Ala Ala Glu Glu Lys Lys Asp
                85                  90                  95
```

-continued

```
Glu Lys Lys Glu Glu Ser Glu Glu Ser Asp Asp Asp Met Gly Phe Gly
                100                 105                 110
Leu Phe Asp
        115

<210> SEQ ID NO 35
<211> LENGTH: 115
<212> TYPE: PRT
<213> ORGANISM: Homo sapiens

<400> SEQUENCE: 35

Met Arg Tyr Val Ala Ser Tyr Leu Leu Ala Leu Gly Gly Asn Ser
1               5                   10                  15

Ser Pro Ser Ala Lys Asp Ile Lys Lys Ile Leu Asp Ser Val Gly Ile
                20                  25                  30

Glu Ala Asp Asp Arg Leu Asn Lys Val Ile Ser Glu Leu Asn Gly
                35                  40                  45

Lys Asn Ile Glu Asp Val Ile Ala Gln Gly Ile Gly Lys Leu Ala Ser
    50                  55                  60

Val Pro Ala Gly Gly Ala Val Ala Val Ser Ala Ala Pro Gly Ser Ala
65                  70                  75                  80

Ala Pro Ala Ala Gly Ser Ala Pro Ala Ala Glu Glu Lys Lys Asp
                85                  90                  95

Glu Lys Lys Glu Glu Ser Glu Glu Ser Asp Asp Asp Met Gly Phe Gly
                100                 105                 110

Leu Phe Asp
        115

<210> SEQ ID NO 36
<211> LENGTH: 78
<212> TYPE: PRT
<213> ORGANISM: Helicobacter pylori

<400> SEQUENCE: 36

Met Ala Leu Phe Glu Asp Ile Gln Ala Val Ile Ala Glu Gln Leu Asn
1               5                   10                  15

Val Asp Ala Ala Gln Val Thr Pro Glu Ala Glu Phe Val Lys Asp Leu
                20                  25                  30

Gly Ala Asp Ser Leu Asp Val Val Glu Leu Ile Met Ala Leu Glu Glu
                35                  40                  45

Lys Phe Asn Ile Glu Ile Pro Asp Glu Gln Ala Glu Lys Ile Val Asn
    50                  55                  60

Val Gly Asp Val Val Lys Tyr Ile Glu Asp Asn Lys Leu Ala
65                  70                  75

<210> SEQ ID NO 37
<211> LENGTH: 123
<212> TYPE: PRT
<213> ORGANISM: Plasmodium sp.

<400> SEQUENCE: 37

Met Phe Val Val Leu Ser Tyr Val Tyr Gly Val Ser Leu Gln Ile Leu
1               5                   10                  15

Lys Lys Lys Arg Ser Asn Gln Val Asn Phe Leu Asn Arg Lys Asn Asp
                20                  25                  30

Tyr Asn Leu Ile Lys Asn Lys Asn Pro Ser Ser Ser Leu Lys Ser Thr
                35                  40                  45

Phe Asp Asp Ile Lys Lys Ile Ile Ser Lys Gln Leu Ser Val Glu Glu
```

```
                    50                  55                  60
Asp Lys Ile Gln Met Asn Ser Asn Phe Thr Lys Asp Leu Gly Ala Asp
65                  70                  75                  80

Ser Leu Asp Leu Val Glu Leu Ile Met Ala Leu Glu Glu Lys Phe Asn
                85                  90                  95

Val Thr Ile Ser Asp Gln Asp Ala Leu Lys Ile Asn Thr Val Gln Asp
            100                 105                 110

Ala Ile Asp Tyr Ile Glu Lys Asn Asn Lys Gln
        115                 120

<210> SEQ ID NO 38
<211> LENGTH: 78
<212> TYPE: PRT
<213> ORGANISM: Pseudomonas sp.

<400> SEQUENCE: 38

Met Ser Thr Ile Glu Glu Arg Val Lys Lys Ile Val Ala Glu Gln Leu
1               5                   10                  15

Gly Val Lys Glu Glu Val Thr Asn Ser Ala Ser Phe Val Glu Asp
                20                  25                  30

Leu Gly Ala Asp Ser Leu Asp Thr Val Glu Leu Val Met Ala Leu Glu
            35                  40                  45

Glu Glu Phe Glu Thr Glu Ile Pro Asp Glu Lys Ala Glu Lys Ile Thr
        50                  55                  60

Thr Val Gln Glu Ala Ile Asp Tyr Ile Val Ala His Gln Gln
65                  70                  75

<210> SEQ ID NO 39
<211> LENGTH: 78
<212> TYPE: PRT
<213> ORGANISM: Escherichia coli

<400> SEQUENCE: 39

Met Ser Thr Ile Glu Glu Arg Val Lys Lys Ile Ile Gly Glu Gln Leu
1               5                   10                  15

Gly Val Lys Gln Glu Glu Val Thr Asn Asn Ala Ser Phe Val Glu Asp
                20                  25                  30

Leu Gly Ala Asp Ser Leu Asp Thr Val Glu Leu Val Met Ala Leu Glu
            35                  40                  45

Glu Glu Phe Asp Thr Glu Ile Pro Asp Glu Glu Ala Glu Lys Ile Thr
        50                  55                  60

Thr Val Gln Ala Ala Ile Asp Tyr Ile Asn Gly His Gln Ala
65                  70                  75

<210> SEQ ID NO 40
<211> LENGTH: 125
<212> TYPE: PRT
<213> ORGANISM: Saccharomyces cerevisiae

<400> SEQUENCE: 40

Met Phe Arg Ser Val Cys Arg Ile Ser Ser Arg Val Ala Pro Ser Ala
1               5                   10                  15

Tyr Arg Thr Ile Met Gly Arg Ser Val Met Ser Asn Thr Ile Leu Ala
                20                  25                  30

Gln Arg Phe Tyr Ser Ala Asn Leu Ser Lys Asp Gln Val Ser Gln Arg
            35                  40                  45

Val Ile Asp Val Ile Lys Ala Phe Asp Lys Asn Ser Pro Asn Ile Ala
        50                  55                  60
```

-continued

```
Asn Lys Gln Ile Ser Ser Asp Thr Gln Phe His Lys Asp Leu Gly Leu
 65                  70                  75                  80

Asp Ser Leu Asp Thr Val Glu Leu Leu Val Ala Ile Glu Glu Glu Phe
                 85                  90                  95

Asp Ile Glu Ile Pro Asp Lys Val Ala Asp Glu Leu Arg Ser Val Gly
            100                 105                 110

Glu Thr Val Asp Tyr Ile Ala Ser Asn Pro Asp Ala Asn
            115                 120                 125

<210> SEQ ID NO 41
<211> LENGTH: 61
<212> TYPE: PRT
<213> ORGANISM: Brassica sp.

<400> SEQUENCE: 41

Asn Leu Ser Phe Asn Leu Gly Arg Ser Ile Pro Thr Arg Leu Ser Val
  1               5                  10                  15

Ser Cys Ala Ala Lys Pro Glu Thr Ile Glu Lys Val Ser Lys Ile Val
                 20                  25                  30

Lys Lys Gln Leu Ser Leu Lys Asp Asp Gln Lys Val Val Ala Glu Thr
             35                  40                  45

Lys Phe Ala Asp Leu Gly Ala Asp Ser Leu Asp Thr Val
         50                  55                  60

<210> SEQ ID NO 42
<211> LENGTH: 109
<212> TYPE: PRT
<213> ORGANISM: Rhodotorula glutinis

<400> SEQUENCE: 42

Met Lys His Val Ala Ala Tyr Leu Leu Leu Val Ser Ala Gly Asn Thr
  1               5                  10                  15

Ser Pro Ser Ala Glu Asp Val Lys Lys Val Leu Ala Ala Ala Asp Ile
                 20                  25                  30

Gln Ala Asp Glu Arg Leu Ser Val Leu Ile Lys Glu Leu Glu Gly Lys
             35                  40                  45

Asp Val Asn Glu Val Ile Ala Glu Gly Ser Lys Lys Leu Ala Ser Val
         50                  55                  60

Pro Ser Gly Gly Ala Ala Pro Ala Ala Ala Gly Gly Ala Ala Ala Ala
 65                  70                  75                  80

Gly Gly Ala Ala Glu Glu Lys Ala Glu Asp Lys Pro Ala Glu Lys Asp
                 85                  90                  95

Glu Glu Ser Asp Asp Asp Met Gly Phe Gly Leu Phe Asp
            100                 105
```